US005866394A

United States Patent [19]

Houtz

[11] Patent Number: 5,866,394

[45] Date of Patent: Feb. 2, 1999

[54] CLONING AND DEVELOPMENTAL EXPRESSION OF PEA RIBULOSE-1,5-BISPHOSPHATE CARBOXYLASE/OXYGENASE LARGE SUBUNIT EPSILON N-METHYLTRANSFERASE

[75] Inventor: Robert L. Houtz, Lexington, Ky.

[73] Assignee: University of Kentucky Research Foundation, Lexington, Ky.

[21] Appl. No.: 741,931

[22] Filed: Oct. 31, 1996

Related U.S. Application Data

[62] Division of Ser. No. 391,000, Feb. 21, 1995, Pat. No. 5,723,752.

[51] Int. Cl.$^6$ .............................. C12N 9/10; C07H 21/04

[52] U.S. Cl. .............................. 435/193; 536/23.2

[58] Field of Search .............................. 435/193; 536/23.2

[56] References Cited

U.S. PATENT DOCUMENTS 5,422,108 6/1995 Mirkov et al. ....................... 424/94.61

OTHER PUBLICATIONS

Ying et al., "Molecular Rationale for the Absence of Methylation at Lysyl Residue 14 in the Large Subunit of Spinach Rubisco", Plant Physiology (Supplement), 111(2): (Jun. 1, 1996).

Wang et al., "Affinity Purification of Ribulose–1,5bisphosphate Carboxylase/Oxygenase Large Subunit εN–Methyltransferase", Protein Expression and Purification 6:528–536 (1995).

Klein et al., "Cloning and Development Expression of PEA Ribulose–1,5–bisphosphate carboxylase/oxygenase Large Subunit N–Methyltransferase", Plant Molecular Biology 27:249–261 (1995).

Houtz et al., "Posttranslation Modifications in the Amino–Terminal Region of the Large Subunit of Ribulose–1.5–Bisphosphate Carboxylase/Oxygenase from Several Plant Species", Plant Physiology, 98:1170–1174 (1992).

Houtz et al., "Post–Translational Modifications in the Large Subunit of Ribulose Bisphosphate Carboxylase/Oxygenase", Proc. Natl. Acad. Sci, USA, 86:1855–1859 (Mar. 1989).

Mulligan et al., "Reaction–intermediate Analogue Binding by Ribulose Bisphosphate Carboxylase/Oxygenase Causes Specific Changes in Proteolytic Sensitivity: The Amino–Terminal Residue of the Large Subunit is Acetylated Proline," Proc. Natl. Acad. Sci., USA, 85:1855–1859 (Mar. 1989).

Black et al., "Light–Regulated Methylation of Chloroplast Proteins", The Journal of Biological Chemistry, vol. 262, No. 20, Jul. 15, 1987, pp. 9803–9807.

Houtz et al., "Affinity Purification of Ribulose–1,5–Bisphosphate Carboxylase/Oxygenase Large Subunit εN–Methyltransferase", Supplement to Plant Physiology, vol. 99, Supp. 1, Aug. 1992, Abstract No. 343.

Houtz et al., "Identification and Specificity Studies of Ribulose–1,5–Bisphosphate Carboxylase/Oxygenase Large Subunit εN–Methyltransferase", Supplement to Plant Physiology, vol. 99, Supp. 1, Aug. 1992, Abstract No. 344.

Houtz et al., "Partial Amino Acid Sequence of Ribulose–1, 5–Bisphosphate Carboxylase/Oxygenase Large Subunit εN–Methyl Transferase", Supplement to Plant Physiology, vol. 102, No. 1, May 1993, Abstract No. 248.

Houtz et al., "Partial Purification and Characterization of Ribulose–1,5–bisphosphate Carboxylase/Oxygenase Large Subunit εN–Methyltransferase", Plant Physiol. vol. 97, No. 3, 1991, pp. 913–920.

Klein et al., "Cloning and Expression of the Rubisco Large Subunit Methyl–Transferase Gene from Pea", Supplement to Plant Physiology, vol. 105, May 1994, Abstract No. 438.

Niemi et al., "Protein Methylation in Pea Chloroplast", Plant Physiol., vol. 93, 1990, pp. 1235–1240.

Napoli et al., "Introduction of a Chimeric Chalcone Synthase Gene into Petunia Results in Reversible Co–Suppression of Homologous Genes in trans", Plant Cell, vol. 2, 1990, pp. 279–289.

Smith et al., "Antisense RNA Inhibition of Polygalacturonase Gene Expression in Transgenic Tomatoes", Nature, vol. 334, 1988, pp. 724–726.

Klein et al., "Cloning and Developmental Expression of the Sucrose–Phosphate–Synthase Gene From Spinach", Planta, vol. 190, No. 4, 1993, pp. 498–510.

Eckes et al., "Isolation and Characterization of a Light–Inducible, Organ–Specific Gene from Potato and Analysis of its Expression after Tagging and Transfer into Tobacco and Potato Shoots", Mol. Gen. Genet., vol. 205, 1986, pp. 14–22.

Klein et al. (1995) Plant Moecular Biology 27, pp. 249–261.

*Primary Examiner*—Robert A. Wax

*Assistant Examiner*—Elizabeth Slobodyansky

*Attorney, Agent, or Firm*—Burns, Doane, Swecker & Mathis, L.L.P.

[57] ABSTRACT

The gene sequence for ribulose-1,5-bisphosphate carboxylase/oxygenase (Rubisco) large subunit (LS) $^{\epsilon}$N-methyltransferase (protein methylase III or Rubisco LSMT) is disclosed. This enzyme catalyzes methylation of the ε-amine of lysine-14 in the large subunit of Rubisco. In addition, a full-length cDNA clone for Rubisco LSMT is disclosed. Transgenic plants and methods of producing same which (1) have the Rubisco LSMT gene inserted into the DNA, and (2) have the Rubisco LSMT gene product or the action of the gene product deleted from the DNA are also provided. Further, methods of using the gene to selectively deliver desired agents to a plant are also disclosed.

4 Claims, 7 Drawing Sheets

FIG. 2A

```
                                         A ACA CAC AAA AGA AAA GCG TAT TAT CAC AAA   31

                                     M   A   T   I   F   S   G   G   S   V   S   P   F   L
ACA AAA CCA AGA ACT AGA AAC CAG AAA ATG GCT ACT ATC TTT TCC GGA GGT TCA GTT TCT CCC TTT CTT   100

 F   H   T   N   K   G   T   S   F   T   Z   K   A   P   I   L   H   L   K   R   S   F   S
TTT CAC ACC AAC AAG GGT ACA TCT TTT ACA ZZZ AAA GCT CCA ATT CTT CAT CTC AAG AGA TCT TTC TCT   169

 A   K   S   V   A   S   V   G   T   E   Z   S   L   S   P   A   V   Q   T   F   W   K   W
GCA AAA TCA GTA GCC TCT GTA GCA ACC GAA ZZZ TCA CTC TCT CCA GCA GTT CAA ACC TTC TGG AAG TGG   238

 L   Q   E   E   G   V   I   T   A   K   Z   P   V   K   A   S   V   V   T   E   G   L   G
CTA CAG GAA GAA GCT GTC ATC ACT GCA AAG ZZZ CCA GTG AAA GCT AGT GTG GTC ACA GAA GGT TTA GGA   307

                                              P16
 L   V   A   L   K   D   I   S   R   N   D   V   I   L   Q   V   P   K   R   L   W   I   N
TTG GTT GCA CTT AAG GAC ATT TCT AGG AAT GAT GTT ATT TTG CAG GTA CCA AAA AGG CTG TGG ATA AAT   376

 P   D   A   V   A   A   S   E   I   G   R   V   C   S   E   L   K   P   W   L   S   V   I
CCA GAT GCA GTT GCA GCT TCA GAG ATT GGG AGA GTG TGC AGT GAG TTG AAG CCA TGG TTG TCT GTT ATA   445

 L   F   L   I   R   E   R   S   R   E   D   S   V   W   K   H   Y   F   G   I   L   P   Q
CTC TTT CTT ATA AGA GAG AGG TCA AGG GAA GAT TCT GTT TGG AAG CAC TAT TTT GGT ATT CTG CCA CAG   514

 E   T   D   S   T   I   Y   W   S   E   E   E   L   Q   E   L   Q   G   S   Q   L   L   K
GAA ACT GAT TCT ACT ATA TAT TGG TCA GAG GAA GAG CTT CAA GAG CTT CAA GGT TCT CAA CTT TTG AAA   583

                                                                                  P15
 T   T   V   S   V   K   E   Y   V   K   N   E   C   L   K   L   E   Q   E   I   I   L   P
ACA ACA GTG TCT GTG AAA GAA TAT GTG AAG AAT GAA TGT TTG AAA CTA GAA CAA GAA ATC ATT CTC CCT   652
```

FIG. 2B

```
N   K   R   L   F   P   D   P   V   T   L   D   D   F   F   W   A   F   G   I   L   R   S
AAT AAG CGG CTT TTT CCG GAT CCT GTG ACG CTG GAT GAC TTC TTT TGG GCA TTT GGA ATT CTC AGA TCA   721

                                                            P14
R   A   F   S   R   L   R   N   E   N   L   V   V   V   P   M   A   D   L   I   N   H   S
AGG GCG TTT TCT CGC CTT CGC AAT GAA AAT CTG GTT GTG GTT CCA ATG GCA GAC TTG ATT AAC CAC AGT   790

                                                                        P16'
A   G   V   T   T   E   D   H   A   V   E   V   K   G   A   A   G   L   F   S   W   D   Y
GCA GGA GTT ACT ACA GAG GAT CAT GCT TAT GAA GTT AAA GGA GCA GCT GGC CTT TTC TCT TGG GAT TAC   859

L   F   S   L   K   S   P   L   S   V   K   A   G   E   Q   V   Y   I   Q   Y   D   L   N
CTA TTT TCC TTA AAG AGC CCC CTT TCC GTC AAG GCC GGA GAA CAG GTA TAT ATA CAA TAT GAT TTG AAC   928

K   S   N   A   E   L   A   L   D   Y   G   F   I   E   P   N   E   N   R   H   A   Y   T
AAA AGC AAT GCA GAG TTG GCT CTA GAC TAC GGT TTC ATT GAA CCA AAT GAA AAT CGA CAT GCA TAC ACT   997

L   T   L   E   I   S   E   S   D   P   F   F   D   D   K   L   D   V   A   E   S   N   G
CTG ACG CTG GAG ATA TCT GAG TCG GAC CCT TTT TTT GAT GAC AAA CTA GAC GTT GCT GAG TCC AAT GGT   1066

                                                P18
F   A   Q   T   A   Y   F   D   I   F   Y   N   R   T   L   P   P   G   L   L   P   Y   L
TTT GCT CAG ACA GCG TAC TTT GAC ATC TTC TAT AAT CGC ACT CTT CCA CCT GGA TTG CTT CCA TAT CTG   1135

R   L   V   A   L   G   G   T   D   A   F   L   L   E   S   L   F   R   D   T   I   W   G
AGA CTT GTA GCG CTA GGG GGT ACC GAC GCT TTC TTA TTG GAA TCA CTG TTC AGA GAC ACC ATA TGG GGT   1204

    P17
H   L   E   L   S   V   S   R   D   N   E   E   L   L   C   K   A   V   R   E   A   C   K
CAT CTT GAG TTG TCT GTC AGC CGT GAC AAT GAG GAG CTA CTA TGC AAA GCC GTT CGA GAA GCC TGC AAA   1273
```

FIG. 2C

```
 S   A   L   A   G   Y   H   T   T   I   E   Q   D   R   E   L   K   E   G   N   L   D   S
TCT GCC CTT GCT GGT TAT CAT ACA ACC ATT GAA CAG GAT CGC GAG TTG AAA GAA GGA AAT CTA GAT TCA   1342

 R   L   A   I   A   V   G   I   R   E   G   E   K   M   V   L   Q   Q   I   D   G   I   F
AGG CTT GCA ATA GCA GTT GGA ATA AGA GAA GGG GAA AAG ATG GTC CTG CAG CAA ATT GAC GGG ATC TTC   1411

 E   Q   K   E   L   E   L   D   Q   L   E   Y   Y   Q   E   R   R   L   K   D   L   G   L
GAG CAG AAA GAA TTG GAG TTG GAC CAG TTA GAG TAT TAT CAA GAA AGG AGG CTC AAG GAT CTT GGA CTT   1480

 C   G   E   N   G   D   I   L   G   D   L   G   K   F   F
TGC GGA GAA AAT GGC GAT ATC CTT GGA GAC CTA GGA AAA TTC TTC TAA TCT TGC AGG AAA ATT CTT CTA   1549
ATC TTG CAG GAA GCA TTT CAA CCT GTT AAA GAT ACA CTG TTG TTT ACA AAT GGA GTC TTC TGA GAC GTA   1618
CGA TGC CAT GAT TTT GCA ATC AAT CTT AAG AGG ATC GTG ATC AAT TTT GAC TCT GGA GTC TGG ACC AAT   1687
CCA TTA CAT GCT TGA AGT TTG TAA AGA GGA AAA TGT AAT GTG TGA AAT ATA AAT TAC ACT TCT GTA CTG   1756
GTG ATT ATT TAT AAA GCA GTT GAC CAT TAT TAT TAC AAA AAA AAA
```

CLONING AND DEVELOPMENTAL EXPRESSION OF PEA RIBULOSE-1,5-BISPHOSPHATE CARBOXYLASE/OXYGENASE LARGE SUBUNIT EPSILON N-METHYLTRANSFERASE

This application is a divisional, of Application No. 08/391,000, filed Feb. 21, 1995 now U.S. Pat. No. 5,723, 752.

IDENTIFICATION OF FEDERAL FUNDING

The present invention was supported by U.S. Department of Energy Grant DE-FG05-92ER20075.

BACKGROUND OF THE INVENTION

1. Field of the Invention

The present invention relates to ribulose-1,5-bisphosphate carboxylase/oxygenase (Rubisco) large subunit (LS) $_{\epsilon}$N-methyltransferase (protein methylase III or Rubisco LSMT). This enzyme catalyzes methylation of the $\epsilon$-amine of lysine-14 in the large subunit of Rubisco. In addition, the present invention relates to a gene and a full-length cDNA clone for Rubisco LSMT, which was isolated utilizing polymerase chain reaction-based technology and conventional bacteriophage library screening. The present invention further relates to transgenic plants and methods of producing same which (1) have the Rubisco LSMT gene inserted into the DNA, and (2) have the Rubisco LSMT gene product deleted. Methods of using the gene to selectively deliver desired agents to a plant are also disclosed.

2. Description of the Related Art

Protein methylation is a widespread and common post-translational modification catalyzed by several different protein methyltransferases (Paik et al, "Protein methylation," in Freedman et al (eds), *The Enzymology of Posttranslational Modifications of Proteins*, vol. 2, pp. 187–228, Academic Press, London (1985)). Proteins which contain trimethyllysyl residues include cytochrome c (Cessay et al, "The relationship between the trimethylation of lysine 77 and cytochrome c metabolism in *Saccharomyces cerevisiae,*" *Int. J. Biochem.* 26(5):721–734 (1994); Cessay et al, "Further investigations regarding the role of trimethyllysine for cytochrome c uptake into mitochondria," *Int. J. Biochem.* 23(7,8): 761–768 (1991); DiMaria et al, "Cytochrome c specific methylase from wheat germ," *Biochemistry* 21:1036–1044 (1982); Farooqui et al, "Effect of Methylation on the Stability of Cytochrome c of *Saccharomyces cerevisiae* in vivo," *J. Biol. Chem.* 256(10):5041–5045 (1981); and Farooqui et al, "In vivo studies on yeast cytochrome c methylation in relation to protein synthesis, " *J. Biol. Chem.* 255(10):4468–4473 (1980)), calmodulin (Han et al, "Isolation and kinetic characterization of the calmodulin methyltransferase from sheep brain, " *Biochemistry* 32:13974–13980 (1993); and Rowe et al, "Calmodulin N-methyltransferase," J. *Biol. Chem.* 261(15):7060–7069 (1986)), histone-H1 (Sarnow et al, "A histone H4-specific methyltransferase properties, specificity and effects on nucleosomal histones," *Biochim. Biophys. Acta* 655:349–358 (1981); and Tuck et al, "Two histone HI-specific protein-lysine N-methyltransferases from *Euglena gracilis,*" *J. Biol. Chem.* 260(11):7114–7121 (1985)), and ribosomal proteins (Chang et al, "Purification and properties of a ribosomal protein methylase from *Escherichia coli* Q13," *Biochemistry* 14(22):4994–4998 (1975); Lobet et al, "Partial purification and characterization of the specific protein-lysine N-methyltransferase of YL32, a yeast ribosomal protein," *Biochim. Biophy. Acta* 997:224–231 (1989)). However, the biological function of post-translational protein methylation in all but a few systems remains obscure. Trimethyllysine can serve as a metabolic precursor to carnitine (Paik et al, "Carnitine biosynthesis via protein methylation," *TIBS* 2: 159–162 (1977)), while carboxyl methylation of bacterial membrane proteins plays a major role in chemotaxis (Clarke, "Protein carboxyl methyltransferases: Two distinct classes of enzymes," *Ann. Rev. Biochem.* 54: 479–506 (1985)). Evidence suggests that methylation of Lys-115 in calmodulin affects certain activities including in vitro NAD kinase activation (Roberts et al, "Trimethyllysine and protein function," *J. Biol. Chem.* 261 (4):1491–1494 (1986)), and in vivo susceptibility to ubiquitination (Gregori et al, "Bacterially synthesized vertebrate calmodulin is a specific substrate for ubiquitination," *J. Biol. Chem.* 262(6):2562–2567 (1987); and Gregori et al, "Specific recognition of calmodulin from *Dictyostelium discoideum* by the ATP ubiquitin-dependent degradative pathway," *J. Biol. Chem.* 260(9):5232–5235 (1985); but see also Ziegenhagen et al, "Multiple ubiquitination of calmodulin results in one polyubiquitin chain linked to calmodulin," *FEBS Lett.* 271(1,2):71–75 (1990); and Ziegenhagen et al, "Plant and fungus calmodulins are polyubiquitinated at a single site in a $Ca^{2+}$-dependent manner," *FEBS Lett.* 273(1,2):253–256 (1990)). Conflicting reports (Farooqui et al, "Effect of Methylation on the Stability of Cytochrome c of *Saccharomyces cerevisiae*in vivo," *J. Biol. Chem.* 256(10):5041–5045 (1981); Frost et al, "Cytochrome c methylation," *Protein methylation*, Ch. 4, pp. 59–76 (1990); and Frost et al, "Effect of enzymatic methylation of cytochrome c on its function and synthesis," *Int. J. Biochem.* 22(10):1069–1074 (1990); versus Cessay et al, "The relationship between the trimethylation of lysine 77 and cytochrome c metabolism in *Saccharomyces cerevisiae,*" *Int. J. Biochem.* 26(5):721–734 (1994); Cessay et al, "Further investigations regarding the role of trimethyllysine for cytochrome c uptake into mitochondria," *Int. J. Biochem.* 23(7, 8):761–768 (1991)) also implicate methylation of Lys-77 in cytochrome c as having a role in protein stability, heme incorporation, and mitochondrial transport. A major limitation to elucidating the biological role of lysine methylation in eukaryotes has been the absence of a protein methylase III gene. Hence, molecular studies of the physiological and biochemical function performed by methylation of protein bound lysyl residues have been restricted to site-directed mutational analysis of the methylation site in the target protein (Ceesay et al, "The relationship between the trimethylation of lysine 77 and cytochrome c metabolism in *Saccharomyces cerevisiae,*" *Int. J. Biochem.* 26(5):721–734 (1994); Cessay et al, "Further investigations regarding the role of trimethyllysine for cytochrome c uptake into mitochondria," *Int. J. Biochem.* 23(7,8):761–768 (1991); and Roberts et al, "Expression of a calmodulin methylation mutant affects the growth and development of transgenic tobacco plants," *Proc. Nat. Acad. Sci. USA* 89:8394–8398 (1992)). These studies have been inconclusive as to the exact biological role of methylation of the $\epsilon$-amine of protein bound lysyl residues.

Ribulose-1,5-bisphosphate carboxylase-oxygenase (Rubisco) catalyzes the reduction of atmospheric $CO_2$ during photosynthesis. A great deal is known about the quaternary structure, catalytic mechanism, active site residues, in vivo regulatory mechanisms, and gene expression for this abundant enzyme, see, for example, Andrews et al, "Rubisco: Structure, Mechanisms, and Prospects for Improvement," in Hatch et al (eds), *The Biochemistry of*

*Plants*, vol. 10, pp. 131–218. Academic Press, New York (1987); Dean et al, "Structure, evolution, and regulation of rbcS genes in higher plants," *Annu. Rev. Plant. Physiol. Plant Mol. Biol.* 40: 415–439 (1989); and Mullet, "Chloroplast development and gene expression," *Annu. Rev. Plant. Physiol. Plant Mol. Biol.* 39: 475–502 (1988). Higher plant Rubisco is a hexadecameric protein composed of eight chloroplast-encoded large subunits (referred to herein as "LS") and eight nuclear-encoded small subunits (referred to herein as "SS"). Synthesis of the LS is accompanied by post-translational processing of the N-terminal domain (Houtz et al, "Post-translational modifications in the large subunit of ribulose bisphosphate carboxylase/oxygenase," *Proc. Natl. Acad. Sci. USA* 86:1855–1859 (1989); and Mulligan et al, "Reaction-intermediate analogue binding by ribulose bisphosphate carboxylase/oxygenase causes specific changes in proteolytic sensitivity: The amino-terminal residue of the large subunit is acetylated proline," *Proc. Natl. Acad. Sci. USA* 85:1513–1517 (1988)). The N-terminal Met-1 and Ser-2 are removed and Pro-3 acetylated. Additionally, the LS of Rubisco from tobacco, muskmelon, pea, and several other species is post-translationally modified by trimethylation of the ϵ-amine of Lys-14 ( Houtz et al "Posttranslational modifications in the amino-terminal region of the large subunit of ribulose-1,5-bisphosphate carboxylase/oxygenase from several plant species," "*Plant Physiol.* 98:1170–1174 (1992); Houtz et al, "Post-translational modifications in the large subunit of ribulose bisphosphate carboxylase/oxygenase," *Proc. Natl. Acad. Sci. USA* 86:1855–1859 (1989)). The enzyme responsible for this latter modification is a highly specific chloroplast-localized S-adenosylmethionine (AdoMet):protein (lys) $^{\epsilon}$N-methyltransferase (protein methylase III, Rubisco LSMT, EC 2.1.1.43). Recently, Rubisco LSMT was affinity purified ~8000-fold from pea chloroplasts and identified as a monomeric protein with a molecular mass of ~57 kDa (Wang et al "Affinity Purification of Ribulose-1,5-bisphosphate Carboxylase/Oxygenase Large Subunit $^{\epsilon}$N-Methyltransferase," accepted by *Protein Expression and Purification* (1995)).

OBJECTS AND SUMMARY OF THE INVENTION

In view of the state of the art as previously described, there thus exists a need in the art for a better understanding of the biological function of post-translational protein methylation in higher plant systems. More specifically, a better understanding of the biological role of methylation of the ϵ-amine of protein bound lysyl residues.

It is thus an object of the present invention to provide a Rubisco LSMT gene.

It is a further object of the present invention to provide the DNA and amino acid sequence for a Rubisco LSMT enzyme.

It is a still further object of the present invention to provide a full-length cDNA clone for Rubisco LSMT.

Another object of the present invention is to determine and selectively manipulate the biological role of lysine methylation in eukaryotes.

In a first aspect, the present invention relates to a Rubisco LSMT gene which is expressed in a higher plant and which encodes Rubisco LSMT. Rubisco LSMT catalyzes methylation of the ϵ-amine of lysine-14 in the LS of Rubisco. A particularly preferred higher plant includes the pea.

In a second aspect, the present invention relates to the DNA and amino acid sequence for a Rubisco LSMT enzyme.

In a third aspect, the present invention relates to a recombinant vector including the Rubisco LSMT gene described above. The vector is suitable for transforming higher plant seed crops.

In a fourth aspect, the present invention relates to an isolated or recombinantly expressed Rubisco LSMT enzyme encoded by the Rubisco LSMT gene described above.

In a fifth aspect, the present invention relates to a method for introducing the Rubisco LSMT gene into a plant which does not possess said gene, which method comprises transforming a higher plant seed crop with the Rubisco LSMT gene vector described above such that the plant expresses the Rubisco LSMT enzyme encoded by the gene.

In a sixth aspect, the present invention relates to a method for selectively eliminating a plant which comprises the Rubisco LSMT gene by deleting the gene product, or eliminating the action of the gene product, from the plant. Without the Rubisco LSMT gene product or the action of the gene product, the plant would be unable to catalyze net $CO_2$ fixation during photosynthesis and would thus die.

In a seventh aspect, the present invention relates to a method for introducing agents to a plant cell which agents will selectively increase or decrease activity of Rubisco.

In a further aspect, the present invention relates to a recombinant or transgenic plant transformed with the Rubisco LSMT gene described above.

BRIEF DESCRIPTION OF THE DRAWINGS

FIG. 1 shows a reverse phase-HPLC of peptic polypeptides from Rubisco LSMT.

FIG. 2, SEQ. ID. NO: 41 illustrates the nucleotide and predicted amino acid sequence of pea rbcMT cDNA. Nucleotide position is marked on the right. The start and stop codons are underlined and segments corresponding to peptic fragments are marked by lines above the amino-acid sequence. The position of amino acids encoded by the PCR-derived partial cDNA is blocked.

Figure 1A:
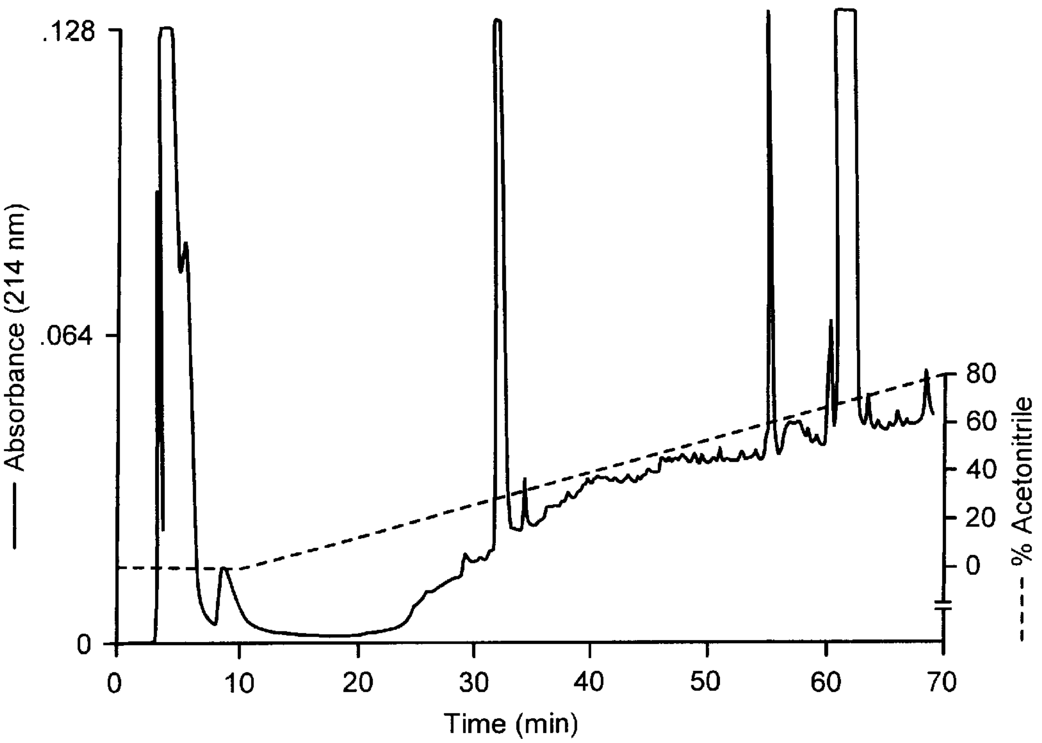
FIG. 1*a* shows the control of peptic digestion of Immobilon-CD membrane without Rubisco LSMT.

Northern blots of rbcS, rbcL, and rbcMT were exposed to x-ray film for 1 hour, 1 hour, and 36 hours, respectively.

DETAILED DESCRIPTION OF THE INVENTION

The present invention relates to a Rubisco LSMT gene, its DNA and amino acid sequence encoding therefor, and a cDNA clone thereof.

In the present application, naturally occurring amino acid residues in peptides are abbreviated as recommended by the IUPAC OIUB Biochemical Nomenclature Commission as follows: Phenylalanine is Phe or F; Leucine is Leu or L; Isoleucine is Ile or I; Methionine is Met or. M; Norleucine is Nle; Valine is Val or V; Serine is Ser or S; Proline is Pro or P; Threonine is Thr or T; Alanine is Ala or A; Tyrosine is Tyr of Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid.

Synthetic or non-naturally occurring amino acids refer to amino acids which do not naturally occur in vivo but which, nevertheless, can be incorporated into the peptide structures described herein. Preferred synthetic amino acids are the D-amino acids of naturally occurring L-amino acids as well as non-naturally occurring D and L amino acids represented by the formula $H_2NCHR^1COOH$, wherein $R^1$ is: (1) a lower alkyl group; (2) a cycloalkyl group of from 3 to 7 carbon atoms; (3) a heterocycle of from 3 to 7 carbon atoms and 1 to 2 heteroatoms selected from the group consisting of oxygen, sulfur, and nitrogen; (4) an aromatic or arylalkyl residue of from 6 to 15 carbon atoms optionally having from 1 to 3 substituents on the aromatic nucleus selected from the group consisting of hydroxyl, lower alkoxy, amino, and carboxyl; (5) alkylene-Y where alkylene is an alkylene group of from 1 to 7 carbon atoms and Y is selected from the group consisting of hydroxy, amino, cycloalkyl of from 3 to 7 carbon atoms, heterocyclic of from 3 to 7 carbon atoms and 1 to 2 heteroatoms selected from the group consisting of oxygen, sulfur and nitrogen, and $—C(O)R^2$ where $R^2$ is selected from the group consisting of hydrogen, lower alkyl, lower alkoxy, and $—NR^3R^4$ where $R^3$ and $R^4$ are independently selected from the group consisting of hydrogen and lower alkyl; (6) alkylene-$S(O)_nR^5$ where n is 1 or 2, and $R^5$ is a lower alkyl or lower alkylene.

Particularly preferred synthetic amino acids include, by way of example, the D-amino acids of naturally occurring L-amino acids, L-1-napthylalanine, L-2-naphthylalanine, L-cyclohexylalanine, L-2-amino isobutyric acid, the sulfoxide and sulfone derivatives of methionine, and the lower alkoxy derivatives of methionine. "Peptide mimetics" are also encompassed by the present invention and include peptides having one or more of the following modifications:

peptides wherein one or more of the peptidyl [—C(O)NH—] linkages (bonds) have been replaced by a non-peptidyl linkage such as carbamate linkage [—OC(O)N<], phosphonate linkage, amidate linkage, sulfonamide linkage, and secondary amine linkage or with an alkylated peptidyl linkage [$C(O)NR^6—$ where $R^6$ is a lower alkyl], peptides wherein the N-terminus is derivatized to a $—NR^7R^8$ group, to a $—NC(O)R^7$ group where $R^7$ and $R^8$ are independently selected from hydrogen and lower alkyls with the proviso that $R^7$ and $R^8$ are both not hydrogen, to a succinimide group, to a benzyloxycarbonyl-NH—(CBZ—NH—) group, to a benzyloxycarbonyl-NH— group having from 1 to 3 substituents on the phenyl ring selected from the group consisting of lower alkyl, lower alkoxy, chloro, and bromo, peptides wherein the C terminus is derivatized to $>C(O)R^9$ where $R^9$ is selected from the group consisting of hydrogen, lower alkyl, lower alkoxy, and $NR^{10}R^{11}$ where $R^{10}$ and $R^{11}$ are independently selected from the group consisting of hydrogen and lower alkyl.

Although the present invention is described with respect to peas, it will be appreciated that the techniques employed herein are applicable to other photosynthesizing plants, e.g., legumes, soybeans, *solanaceae* (tomato, potato, tobacco, pepper) and *cucurbitaceae* (cucumbers, melons, gourds). The protein methylase III of other photosynthesizing plants would be expected to exhibit homologous amino acid sequences to those described herein. As described herein, certain aspects of the present invention are applicable to plants not having the Rubisco LSMT gene, e.g., spinach, wheat, corn, lower plants such as algae, monocots (cereals) and the like.

Ribulose-1,5-bisphosphate carboxylase/oxygenase (Rubisco) large subunit (LS) $^{\epsilon}$N-methyltransferase (referred to herein as "Rubisco LSMT") catalyzes methylation of the ε-amine of lysine-14 in the LS of Rubisco. Rubisco is the world's most abundant protein, and serves as the only significant link between the inorganic and organic carbon pools in the Earth's biosphere by catalyzing the reduction of atmospheric carbon dioxide to carbohydrates during photosynthesis. Perturbations of Rubisco activity translate directly into similar changes in plant growth and yield. Thus, there is significant interest in the art in the potential manipulation and control of Rubisco activity through genetic engineering.

However, the complexity and multimeric nature of Rubisco have proven to be substantial obstacles to achieving this goal, which have not yet been overcome. Rubisco LSMT provides an opportunity for the selective manipulation of Rubisco activity through changes in the structure and stability of the N-terminal region in the LS, an area known to be essential for catalytic activity. Rubisco LSMT is a highly specific enzyme which is found to interact only with Rubisco and does not interact with any other protein in the plant cell. Since Rubisco catalyzes the reduction of atmospheric $CO_2$ during photosynthesis, Rubisco and Rubisco LSMT are critical to the plant cell for viability. Furthermore, the exceptionally tight and specific nature of the interaction between Rubisco LSMT and des(methyl) forms of Rubisco creates the possibility for the development of novel synthetic polypeptide herbicides, whose target is the in vivo interaction between Rubisco LSMT and Rubisco, whose specificity crosses a group of plant species related only by the presence of Rubisco LSMT, and whose target protein has no homologue in the entire animal kingdom. Finally, this same affinity of Rubisco LSMT for des(methyl) forms of Rubisco also creates the possibility for the site and protein specific delivery of compounds into the chloroplast and to Rubisco, for the potential manipulation of Rubisco activity and/or stability.

With limited internal amino acid sequence information obtained from high performance liquid chromatography (HPLC)-purified peptic polypeptides from Rubisco LSMT, a full-length cDNA clone was isolated by the present inventor utilizing polymerase chain reaction (PCR)-based technology and conventional bacteriophage library screening. PCR techniques are disclosed, for example, in Klein et al, "Cloning and Developmental Expression of the Sucrose-Phosphate-Synthase Gene From Spinach," *Planta*

190:498–510 (1993); in Ampli-Taq PCR kit by Perkin Elmer—Cetus, Emeryville, Calif.); and in the manufacturer's instruction manual. Bacteriophage library screening is described, for example, in Gantt et al, "Transfer of rp122 to the Nucleus Greatly Preceded its loss from the Chloroplast and Involved the Gain of an Intron," *EMBO J.* 10:3073–3078 (1991), and in the information provided by the manufacturer of the screening membrane (Stratagene, La Jolla, Calif.).

The 1802-base-pair cDNA of Rubisco LSMT encodes a 489-amino acid polypeptide with a predicted molecular mass of ~55 kDa. To the knowledge of the present inventor, this is the first reported DNA and amino acid sequence for a protein methylase III enzyme. A derived N-terminal amino acid sequence of the polypeptide with features common to chloroplast transit peptides was identified. The deduced sequence of Rubisco LSMT did not exhibit regions of significant homology with other protein methyltransferases known in the art, e.g., D-aspartyl/L-isoaspartyl protein methyltransferase (Kagan et al, "Widespread occurrence of three sequence motifs in diverse S-adenosylmethionine-dependent methyltransferases suggests a common structure for these enzymes," *Arch. Biochem. Biophy.* 310(2):417427 (1994)). Widespread occurrence of three sequence motifs in diverse S-adenosylmethionine dependent methyltransferases suggest a common structure for these enzymes. Southern blot analysis of pea genomic DNA indicated a low gene copy number of Rubisco LSMT in pea. A "low gene copy number" indicates that Rubisco LSMT may be encoded by a single gene. Northern analysis revealed a single mRNA species of about 1.8 kb encoding for Rubisco LSMT which was predominately localized in leaf tissue. Illumination of etiolated pea seedlings showed that the accumulation of Rubisco LSMT mRNA is light-dependent. Maximum accumulation of Rubisco LSMT transcripts occurred during the initial phase of light-induced leaf development which preceded the maximum accumulation of rbcS and rbcL mRNA. Transcript levels of Rubisco LSMT in mature light-grown tissue were similar to transcript levels in etiolated tissues indicating that the light-dependent accumulation of Rubisco LSMT mRNA is transient.

A cDNA of the Rubisco LSMT gene from pea was isolated and studies of Rubisco LSMT gene expression initiated. Utilizing amino acid sequence information derived from purified peptic polypeptide fragments from proteolyzed Rubisco LSMT, a full-length cDNA of Rubisco LSMT was obtained. The cDNA of Rubisco LSMT, rbcMT, was used to examine organ-specific and developmental parameters affecting rbcMT gene expression. The expression of two well characterized gene families, rbcS (SS of Rubisco) and rbcL (LS of Rubisco), were also examined to determine if rbcMT expression is coregulated with that of the Rubisco subunit genes, particularly the LS.

The present specification details the purification of peptic fragments from pea Rubisco LSMT and a PCR-based cloning strategy for isolating a full-length cDNA. A similar strategy was previously utilized to obtain a full-length cDNA of sucrose-phosphate synthase from spinach (Klein et al, "Cloning and developmental expression of the sucrose-phosphate-synthase gene from spinach," *Planta.* 190:498–510 (1993)). The low abundance of Rubisco LSMT in pea leaves (~0.01%) prompted the use of PCR, since it would be more difficult to obtain enough protein to ensure the production of an antibody with high-titer and specificity with which to screen a library. Further, the protein sequence information obtained from peptic fragments permitted the confirmation of clones encoding for Rubisco LSMT. Hence, a molecular probe of the pea rbcMT gene was rapidly obtained thereby permitting identification of protein and nucleotide sequence, and characterization of rbcMT gene expression.

To date, the deduced amino-acid sequence of Rubisco LSMT represents the first reported example of a protein $^{\epsilon}$N-methyltransferase. Thus, it is now possible to extend the comparison of known enzyme sequences to include this class of methyltransferases. Interestingly, the deduced amino acid sequence of Rubisco LSMT does not possess any of the three sequence motifs proposed by Kagan and Clarke (Kagan et al, "Widespread occurrence of three sequence motifs in diverse S-adenosylmethionine-dependent methyltransferases suggests a common structure for these enzymes," *Arch. Biochem. Biophy.* 310(2):417–427 (1994)) for methyltransferases. However, knowledge of methyltransferase sequences is still fragmentary and no sequences are yet available for protein arginine, histidine, or N-terminal amino methyltransferases. As noted by Kagan and Clarke, methyltransferases whose sequences are available represent less than one-third of these enzymes and a number of other methyltransferases apparently do not possess the proposed motifs or any additional elements of sequence similarity. Furthermore, several lines of evidence suggest that Rubisco LSMT exclusively methylates the large subunit of Rubisco (Houtz et al, "Posttranslational modifications in the amino-terminal region of the large subunit of ribulose-1,5-bisphosphate carboxylase/oxygenase from several plant species," *Plant Physiol.* 98:1170–1174 (1992); and Houtz et al, "Partial purification and characterization of ribulose- 1,5-bisphosphate carboxylase/oxygenase large subunit $^{\epsilon}$N-methyltransferase," *Plant Physiol.* 97:913–920 (1991)). This high level of specificity may in part explain the lack of overall homology with other methyltransferases. Hence, sequence determination of other yet-to-be-discovered protein(lys)$^{\epsilon}$N-methyltransferases may be necessary to identify conserved, functionally essential regions in this class of enzyme.

Several lines of evidence indicate that there is a low copy number of the rbcMT gene in pea. Genomic Southern blot analysis revealed simple hybridization patterns. DNA sequence information of several cDNA clones revealed an invariant nucleotide sequence in the coding and noncoding regions. Although these observations do not preclude the existence of multiple structural genes encoding Rubisco LSMT, they are consistent with a low- or even single-copy gene hypothesis.

Many plant genes are expressed in a highly regulated manner. Gene products may be present only in certain cell types, at specific stages of development or only following the application of distinct environmental stimuli (Kuhlemeier et al, "Regulation of gene expression in higher plants," *Annu. Rev. Plant Physiol.* 38:221–257 (1987)). In addition, the expression of nuclear genes encoding plasmid proteins is often coordinated with the expression of plastid-encoded protein subunits (Rapp et al, "Chloroplast transcription is required to express the nuclear genes rbcS and cab," *Plant Mol. Biol.* 17:813–823 (1991)). The present specification shows that rbcMT gene expression is regulated in an organ-specific manner at the level of transcription or mRNA stability. The organ-specific expression of rbcMT paralleled that of rbcS and rbcL being predominately localized to photosynthetic leaf tissue. Examination of transcript levels during the light-induced development of etiolated pea leaves indicated that accumulation of mRNA encoding for rbcS, rbcL, and rbcMT is light-dependent. However, the activation of rbcMT expression preceded the maximum accumulation of mRNA encoding for either of the Rubisco subunits. Maximum transcript levels for rbcMT were obtained in the first 24 hours of illumination, which corresponded with the initial, light-dependent phase of rbcS and rbcL transcript accumulation. Interestingly, the kinetics of Rubisco activase mRNA accumulation during the greening of etiolated barley was similar to that reported here for rbcMT mRNA (Zielinski et al, "Coordinate expression of rubisco activase and rubisco during barley leaf cell development," *Plant Physiol.* 90:516–521 (1989)). The present inventor also observed that in continuously illuminated pea leaves rbcMT transcript levels were equal to the levels observed in dark-grown leaves (FIG. 5), while the activity of Rubisco LSMT was nearly 3-fold higher. Since the relative amounts of rbcMT transcripts increased dramatically during the initial phase of light-induced development of etiolated pea leaves and then declined to a level equal to those observed in the dark, changes in the level of Rubisco LSMT protein may be controlled by the level of rbcMT transcripts.

Finally, while a number of $^{\epsilon}$N-methylated lysyl residues in several proteins have been described, no unifying hypothesis with regards to the functional significance of methylated lysyl residues has been discovered. Molecular studies have approached this topic by engineering amino acid substitutions at the position of the methylated lysyl residue in calmodulin (Roberts et al, "Expression of a calmodulin methylation mutant affects the growth and development of transgenic tobacco plants," *Proc. Nat. Acad. Sci. USA* 89:8394–8398 (1992)) and cytochrome c (Cessay et al, "The relationship between the trimethylation of lysine 77 and cytochrome c metabolism in *Saccharomyces cerevisiae,*" *Int. J. Biochem.* 26(5):721–734 (1994); and Cessay et al, "Further investigations regarding the role of trimethyllysine for cytochrome c uptake into mitochondria," *Int. J. Biochem.* 23(7,8):761–768 (1991)), followed by expression of these mutant proteins in transformed tobacco plants and yeast cells, respectively. While the mutated calmodulin and cytochrome c proteins were incapable of acting as substrates for methylation, these studies were inconclusive as to a clear role for site-specific methylation of the target lysyl residues by the calmodulin or cytochrome c protein specific $^{\epsilon}$N-methyltransferases.

The present invention also relates to a method for introducing the Rubisco LSMT gene into a plant which does not possess said gene, such as *Arabidopsis thaliana*. The methods employed for transforming the plants are generally known in the art. For example, the transformation method described in Bechtold et al, *Planta Agrobacterium Mediated Gene Transfer By Infiltration of Adult Arabidopsis Thaliana Plants*, C.R. Acad. Sci., Paris 316:1194–1199 (1993) and Valvekens et al, "*Agrobacterium tumefaciens*-mediated transformation of *Arabidopsis thaliana* root explants by using kanamycin selection," *Proc. Natl. Acad. Sci. USA* 85:5536–5540 (1988), may be used in the method of the present invention. More specifically, the method contemplated herein comprises transforming a plant with the Rubisco LSMT gene vector described above such that the plant expresses the Rubisco LSMT enzyme encoded by the gene. These methods produce transgenic plants, which will have Rubisco LSMT activity and Lys-14 methylation in the LS of Rubisco.

Further, the present invention provides a method for deleting the Rubisco LSMT gene product or the action of the gene product in a photosynthesizing plant which has the Rubisco LSMT gene. Knowing the DNA sequence of the Rubisco LSMT gene, transgenic plants can be constructed expressing antisense RNA to Rubisco LSMT which results in the down-regulation of the Rubisco LSMT gene product, by methods as set forth for example, in Eguchi et al, "Antisense RNA," *Annu. Rev. Biochem.* 60:631–652 (1991). Since the Rubisco LSMT enzyme is essential for Rubisco activity, the deletion of the enzyme would be expected to be lethal to the plant since it would be unable to catalyze net $CO_2$ fixation during photosynthesis. This method, and variations of this method, could thus be used as a herbicide to selectively eliminate photosynthesizing plants.

Due to the high specificity of Rubisco LSMT for Rubisco, knowledge of the sequence for the Rubisco LSMT gene can be used to introduce agents to a plant cell which agents will selectively increase or decrease the activity of Rubisco. Additionally, in this regard, a recombinant vector comprising the sequence of the Rubisco LSMT gene responsible for the tight interaction of Rubisco LSMT with Rubisco could be constructed. Additional agents which enhance or reduce the activity of Rubisco, for example, CA1P (carboxyarabinitol-1-phosphate), CABP (carboxyarabinitol bisphosphate), carbamates and divalent metal cations, are then conjugated to the vector. The vector is then inserted into the plant cell by methods known in the art. The agents will then be delivered to Rubisco as a result of the high specificity and strong interaction of Rubisco LSMT and Rubisco. These agents may be synthetically derived polypeptides that are direct representations of the sequence of amino acids responsible for the interaction of Rubisco LSMT with Rubisco. These synthetic polypeptides would delete Rubisco LSMT activity and result in plant death in the aforementioned manner.

Moreover, the particular sequence disclosed herein for the pea Rubisco LSMT gene may be used to determine the particular sequence in other photosynthesizing plants. The sequence of the gene may be used as a probe to screen cDNA or genomic DNA libraries from other plants and, due to the expected homology between the gene sequences in the various plant species, the particular sequence for the Rubisco LSMT gene in other species may then be found.

In a further aspect, the present invention relates to a recombinant or transgenic plant transformed with the Rubisco LSMT gene described above.

Having now generally described this invention, the same will be better understood by reference to certain specific examples, which are included herein for purposes of illustration only and are not intended to be limiting of the invention or any embodiment thereof, unless so specified.

EXAMPLES

Example 1

Plant Growth

Controlled environment-cultured peas (*Pisum sativum*) were germinated and maintained in environmental chambers as described in Wang et al, *Protein Expression and Purification.* For developmental studies, seeds were either germinated at 23° C. in a dark chamber located in a light-tight room or were grown in an illuminated chamber with a light intensity of 300 $\mu mol \cdot m^{-2} \cdot s^{-1}$ (incandescent plus fluorescent). After 8 days of growth in complete darkness, pea seedlings were either harvested into liquid nitrogen or were transferred to an illuminated chamber for a predetermined period prior to harvest.

Example 2

Purification and assay of Rubisco LSMT

Rubisco LSMT was affinity purified utilizing immobilized spinach Rubisco as describe in Wang et al, cited supra. Briefly, purified spinach Rubisco (McCurry et al, "Ribulose- 1,5-bisphosphate carboxylase/oxygenase from spinach, tomato or tobacco leaves," *Methods in Enzymology* 90(82) :515–521 (1982)) was immobilized to PVDF membranes (Millipore Corp., Bedford, Mass. USA, 60 mg Rubisco/450 $cm^2$) which were then incubated for 4 h at 4° C. with pea chloroplast lysates (20 ml at 20 mg/ml protein per 450 $cm^2$ membrane). After incubation, the PVDF membranes were washed with 50 mM TRIS-HCl (pH 8.2), 5 mM $MgCl_2$, 1 mM EDTA, 0.4M NaCl and subsequently eluted with 20 ml of 50 mM TRIS-HCl (pH 8.2), 5 mM $MgCl_2$, 200 $\mu$M AdoMet and 50 $\mu$g/ml β-lactoglobulin per 450 $cm^2$ membrane. The eluent was concentrated by centrifugal ultrafiltration to a final volume of ~50 $\mu$l and used as a source for purified Rubisco LSMT. The yield from a single PVDF membrane containing immobilized spinach Rubisco was typically 7–10 $\mu$g of purified Rubisco LSMT. Assays of Rubisco LSMT activity were as previously described (Houtz et al, "Partial purification and characterization of ribulose-1,5-bisphosphate carboxylase/oxygenase large subunit $^{\epsilon}$N-methyltransferase," *Plant Physiol.* 97:913–920 (1991)).

Example 3

Peptide profiles and sequence analysis

To separate affinity-purified Rubisco LSMT from the β-lactoglobulin carrier protein, Rubisco LSMT was resolved by SDS-PAGE (10% acrylamide) prior to electrophoretic transfer to Immobilon-CD membranes (Millipore Corp., Bedford, Mass. USA). Conditions for the electrophoretic transfer, visualization and subsequent in vitro enzymatic cleavage of Rubisco LSMT with pepsin were as described, for example, by Paik et al, "Protein methylation," in Freedman et al (eds), *The Enzymology of Posttranslational Modifications of Proteins,* vol. 2, pp. 187–228, Academic Press, London (1985). Peptic peptides released from Rubisco LSMT were isolated by reverse phase-HPLC using conditions described in Patterson et al, "High-yield recovery of electroblotted proteins and cleavage fragments from a cationic polyvinylidene fluoride-based membrane," *Anal. Biochem.* 202:193–203 (1992), with an Aquapore RP-300 7 micron particle size octyl reverse phase column (2.1 mm×220 mm, Applied Biosystems, San Jose, Calif. USA). Peptic peptides were manually collected based on absorbance at 214 nm and samples reduced in volume to ~50 $\mu$l under vacuum. Amino-acid sequence analyses were performed by the Macromolecular Structure Analysis Facility at the University of Kentucky, Lexington, using an Applied Biosystems 477A automated sequencer. For additional confirmation of amino acid sequence data, a duplicate sample of Rubisco LSMT was purified, proteolyzed, and peptic polypeptide fragments submitted for amino acid sequence analyses.

Example 4

Synthesis of first-strand cDNA and polymerase chain reaction amplification

Pools of oligonucleotide primers encoding portions of two LSMT peptic peptides, P14 and P18, were synthesized with the number of different species (degeneracies) in each pool minimized as previously described (Klein et al, "Cloning and developmental expression of the sucrose-phosphate-synthase gene from spinach," *Planta.* 190:498–510 (1993)). First strand cDNA synthesis and polymerase chain reaction (PCR) conditions were as described, for example, in Klein et al, "Cloning and developmental expression of the sucrose-phosphate-synthase gene from spinach," *Planta.* 190:498–510 (1993), except 5 $\mu$l of first strand cDNA was used as PCR-template and the PCR-annealing temperature was reduced to 48° C. The appropriate sense and antisense PCR-primers directed against LSMT peptides, P14 and P18, are shown in Table 1, as shown below.

TABLE 1

Degenerate PCR primer pools designed according to amino-acid sequence of Rubisco LSMT peptides P14 and P18. Underlined nucleotides represent degeneracy nearest 3' terminus at which pools of primers differ.

PEPTIDE P14

$NH_2$—Pro—Met—Ala—Asp—Leu—Ile—Asn—His—Ser—Ala—Gly—Val—Thr—Asn—Glu—Asp—COOH

| | | | | | | | | | | | | | | | | | |
|---|---|---|---|---|---|---|---|---|---|---|---|---|---|---|---|---|---|
| Sense | 5'-CCA | ATG | GCA | GAT | TTA | ATT | AAT | CAT | TCA | GCA | GGA | GTA | ACA | AAT | GAA | GAT-3' | |
| DNA | C | | C | C | G | A | C | C | C | C | C | C | C | C | G | C | |
| | G | | G | | CTA | C | | | G | G | G | G | G | | | | |
| | T | | T | | C | | | | T | T | T | T | T | | | | |
| | | | | | G | | | | AGT | | | | | | | | |
| | | | | | T | | | | C | | | | | | | | |
| P14s1 | | | | 5'-GAT | TTI | ATI | AAT | CAT | ICI | GCI | GGI | GTI | ACI | AAT | GAA | GAT-3' | |
| P14s2 | | | | | | | | | G | | | | | C | G | C | |
| | 3'-GGG | TAC | CGT | CTA | AAT | TAA | TTA | GTA | AGT | CGT | CCT | CAT | TGT | TTA | CTT | CTA-5' | Antisense |
| | C | | G | G | C | T | G | G | G | G | G | G | G | G | C | G | DNA |
| | A | | C | | GAT | G | | | C | C | C | C | C | | | | |
| | T | | A | | G | | | | A | A | A | A | A | | | | |
| | | | | | C | | | | TCA | | | | | | | | |
| | | | | | A | | | | G | | | | | | | | |
| | | 3'-TAC | CGG | CTA | GAI | TAI | TTG | GTG | IGI | CGI | CCI | CAI | TGI | TTG-5' | | | P14a1 |
| | | | C | G | | | | | C | | | | | | | | P14a2 |
| | | | A | | | | | | | | | | | | | | P14a3 |
| | | | T | | | | | | | | | | | | | | P14a4 |

PEPTIDE P18

$NH_2$—Tyr—Asn—Arg—Thr—Leu—Pro—Pro—Gly—Leu—Leu—Pro—Tyr—Leu—Arg—COOH

TABLE 1-continued

Degenerate PCR primer pools designed according to amino-acid sequence of
Rubisco LSMT peptides P14 and P18. Underlined nucleotides represent degeneracy
nearest 3' terminus at which pools of primers differ.

| Sense DNA | 5'-TAT | AAT | CGA | ACA | TTA | CCA | CCA | GGA | TTA | TTA | CCA | TAT | TTA | CGA-3' | |
|---|---|---|---|---|---|---|---|---|---|---|---|---|---|---|---|
| | C | C | C | C | G | C | C | C | G | G | C | C | G | C | |
| | | | G | G | CTA | G | G | G | CTA | CTA | G | | CTA | G | |
| | | | T | T | C | T | T | T | C | C | T | | C | T | |
| | | | AGA | | G | | | | G | G | | | G | AGA | |
| | | | G | | T | | | | T | T | | | T | G | |
| P18s$_1$ | | 5'-AAT | CGI | ACI | TTI | CCI | CCI | GGI | TTI | TTI | CCA | TAT | TT-3' | | |
| P18s$_2$ | | | A | | | | | | | | C | C | C̲ | | |
| | | | | | | | | | | | G | | | | |
| | | | | | | | | | | | T | | | | |
| | 3'-ATA | TTA | GCT | TGT | AAT | GGT | GGT | CCT | AAT | AAT | GCT | ATA | AAT | GCT-5' | Antisense DNA |
| | G | G | G | G | C | G | G | G | C | C | G | G | C | G | |
| | | | C | C | GAT | C | C | C | GAT | GAT | C | | GAT | C | |
| | | | A | A | G | A | A | A | G | G | A | | G | A | |
| | | | TCT | | C | | | | C | C | | | C | TCT | |
| | | | C | | A | | | | A | A | | | A | C | |
| | 3'-ATA | TTA | GCI | TGI | GAI | GGI | GGI | CCI | GAI | GAI | GGI | ATG-5' | | | P18a$_1$ |
| | G̲ | G | T | | | | | | | | | | | | P18a$_2$ |

Following amplification, the PCR product was purified and blunt-end ligated into the SK plasmid (Stratagene, La Jolla, Calif. USA) and sequenced as described, for example, in Klein et al, "Photoaffinity labeling of mature and precursor forms of the small subunit of ribulose-1,5-bisphosphate carboxylase/oxygenase after expression in *Escherichia coli*," *Plant Physiol.* 98:546–553 (1992).

Example 5
Screening of a pea cDNA library

To obtain a full-length cDNA of pea LSMT, a pea λgt10 cDNA library (Gantt et al, "Transfer of rp122 to the nucleus greatly preceded its loss from the chloroplast and involved the gain of an intron," *EMBO J* 10:3073–3078 (1991)) was screened with the Rubisco LSMT-PCR product. Approximately 5×10$^4$ primary plaques were screened with a randomly labeled 360-bp PCR product of Rubisco LSMT under recommended conditions (Stratagene, La Jolla, Calif. USA). After four rounds of plaque purification, three potential positive plaques were identified. Following amplification and purification of bacteriophage DNA, Rubisco LSMT cDNAs were subcloned into SK plasmid and the complete sequence of all three clones (approximately 1600 to 1775 bp in length) was obtained.

The technique of PCR-RACE (Rapid Amplification of cDNA Ends) was used to obtain a portion of the 5'-region of LSMT essentially as described by the manufacturer (GIBCO-BRL. Gaithersburg, Md. USA) except 100-ng of poly(A) mRNA was substituted for total RNA. The gene-specific (antisense) primer used to prime synthesis of first-strand LSMT cDNA was 5'-CCAAAAGAAGTCATC CAGCGTCAC (See FIG. 2, position 700–667 bp). Amplification by PCR used the Anchor primer (supplied by GIBCO-BRL) and a second antisense LSMT-specific primer (5'-CAUCAUCAUCAUCCTGTGGCAGAATACCAAAA TAGT) which annealed to an internal, nested site within the LSMT cDNA (SEQ. ID. NO: 41, position 515–492 bp). The inclusion of the (CAU)$_4$ repeat sequence at the 5' terminus permitted a uracil DNA glycosylase (UDG) cloning strategy of the PCR-RACE product. PCR amplification conditions were as above except for an annealing temperature of 55° C. and an extension time of 40 seconds.

Example 6
Northern blot analyses

Polyadenylated mRNA (0.5 μg per lane) or total RNA (2 μg per lane) was loaded on formaldehyde gels (Sambrook et al, *Molecular cloning: A laboratory manual*, Cold Spring Harbor Laboratory Press, Cold Spring Harbor, N.Y. (1989)) and transferred to GeneScreen nylon membranes (DuPont-NEN, Wilmington, Del. USA). Conditions for prehybridization and hybridization with radiolabeled antisense-RNA probes were as described in Klein et al, "Cloning and developmental expression of the sucrose-phosphate-synthase gene from spinach," *Planta.* 190:498–510 (1993). The northern probe for rbcS was as also described in Klein et al, supra; and Klein et al, "Photoaffinity labeling of mature and precursor forms of the small subunit of ribulose-1,5-bisphosphate carboxylase/oxygenase after expression in *Escherichia coli*," *Plant Physiol.* 98:546–553 (1992)); the probe for rbcL was as described in Klein et al, "Light-induced Transcription of Chloroplast Genes," *J. Biol. Chem.* 265(4):1895–1902 (1990)). The probe for rbcMT was a 1750-base antisense RNA from a portion of the open reading frame and 3'-untranslated region of pea.

Example 7
Genomic Southern blot analyses

Nuclear DNA was isolated from nuclei as described in Bedbrook, "A plant nuclear DNA preparation procedure," *Plant Mol. Biol. Newslett.* 2:24 (1981). Ten μg of high molecular weight DNA was digested to completion with EcoR I, Hind III, and Dra I (50 units each). Following digestion, DNA was ethanol precipitated, electrophoresed on 0.8% agarose gels and transferred to Nytran nylon membranes using an alkaline transfer solution as described (Turboblotter instruction manual, Schleicher and Schuell, Keene, N.H. USA). Blots were prehybridized and hybridized at 42° C. in the presence of 50% formamide and 10% dextran sulfate. The probe was a random primer-labeled 1775 bp cDNA of pea LSMT (encompassing the open reading frame and entire 3'-untranslated region).

Example 8

Computer alignment of the amino acid sequences was performed using the FastDB program (Intelligenetics Inc., Mountain View, Calif. USA). Autoradiograms were scanned with an image acquisition densitometer (BioImage, Milligen/Biosearch, Ann Arbor, Mich. USA) to determine the relative intensity of mRNA signal and quantified on the basis of whole-band analysis.

Figure 1B:
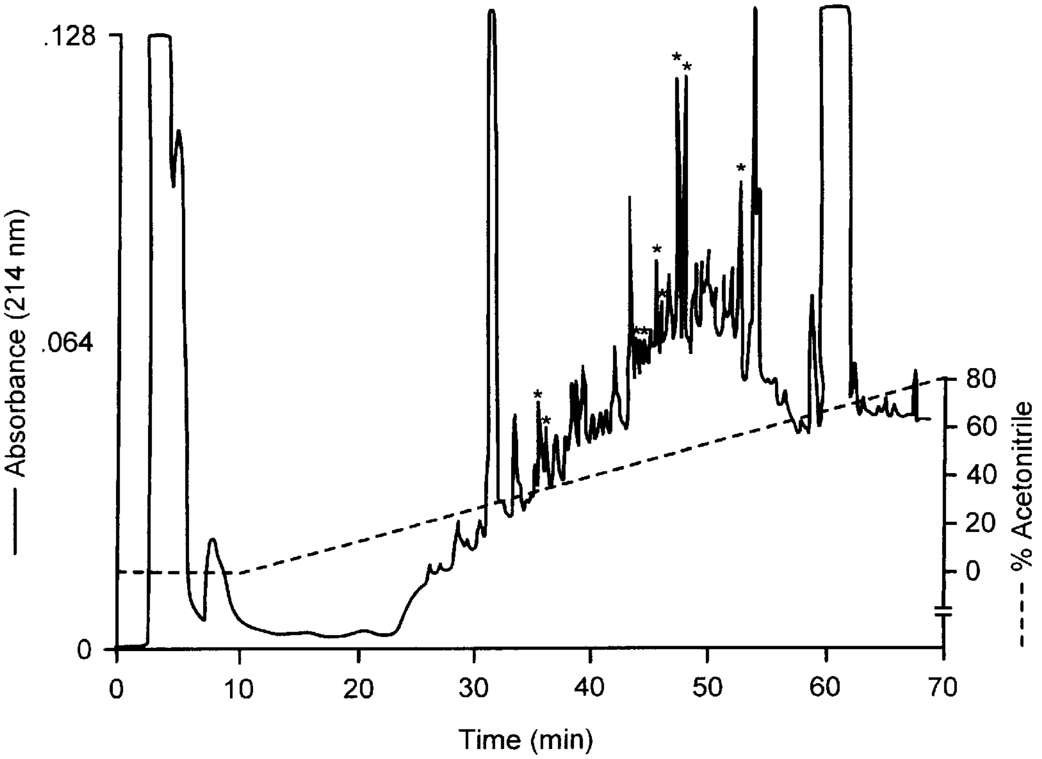
FIG. 1*b* shows the peptic digestion of affinity-purified Rubisco LSMT (~30 μg) electroblotted to Immobilon-CD membrane as described in the Examples. The asterisks identify peaks with $A_{214}$ absorbance which were collected and submitted for amino acid sequence analyses.

In accordance with the present invention, rubisco LSMT has thus been purified ~8000-fold by a novel affinity purification technique from pea chloroplasts as described in Wang et al, *Protein Expression and Purification. After affinity-purification of Rubisco LSMT, SDS-PAGE analysis showed a single polypeptide with an apparent molecular mass of* ~57 kDa. Direct Edman degradative sequencing attempts followed by amino acid analyses after HCl hydrolysis of electroblotted affinity-purified Rubisco LSMT revealed that the N-terminus was blocked. Thus, subsequent efforts were directed towards the acquisition of internal amino acid sequence as a starting point for isolating a cDNA of pea Rubisco LSMT. Reverse phase-HPLC isolation of peptic fragments from Rubisco LSMT resulted in the identification of several reliable amino acid sequences (FIG. 1, asterisks). One polypeptide peak, however, was heterogeneous and consisted of at least three subsequences which were identifiable based on differences in the relative amino acid yields after each cycle of sequencing.

Example 9

The partial amino-acid sequence of Rubisco LSMT enabled the inventor to develop a molecular probe for the Rubisco LSMT gene (rbcMT) using PCR. Pools of deoxyinosine-containing primers encoding part of two peptic peptides, P14 and P18, were synthesized with the number of species in each pool minimized, as shown in Table 1, supra. Using random-hexamer-primed first strand cDNA as a template, the combination of primer pools P14-2s with P18-1a or P18-2a directed the synthesis of a single 360-bp PCR product. No other primer combinations yielded a detectable PCR product.

The fact that either antisense primer P18-1a or P18-2a (which differ by a single nucleotide near the 3' terminus) directed the synthesis of a PCR product reflects the relative tolerance of the PCR system for base-pair mismatches near the 3' terminus of the primer. The identity of the amplification product as a partial cDNA of rbcMT was confirmed by comparison of the deduced amino-acid sequence of the PCR product with additional peptic fragments from purified pea Rubisco LSMT protein (see FIG. 2).

The PCR-amplified fragment of rbcMT was used to screen a λgt10 pea cDNA library (Gantt et al, "Transfer of rp122 to the nucleus greatly preceded its loss from the chloroplast and involved the gain of an intron," *EMBO J* 10:3073–3078 (1991)). Three partial clones were obtained with inserts greater than 1600 bp in length. Complete sequence analysis of the three clones showed that the nucleotide sequence of all clones were identical. The sequence of the PCR-derived cDNA was identical to the λgt10 cDNAs except for the incorrect identification of Thr-249 as an Asn during peptide sequencing of pepsin fragment P14. The longest clone (1775 bp in length) lacked only a portion of the 5'-untranslated region. The remainder of the 5'-untranslated region was obtained by PCR-RACE. The 515 bp PCR-RACE product was barely detectable on ethidium-stained gels which likely reflects the low abundance of the rbcMT mRNA in pea. Sequence analysis confirmed the identity of the PCR-RACE product as encoding for the predicted 5' portion of rbcMT including the remainder of the 5'-untranslated region. In the region where the PCR-RACE product overlapped the cloned cDNA of rbcMT, complete sequence identity was observed (SEQ. ID. NO: 41, position 31–484 bp). Given these overlapping clones, the present inventor was able to assemble the sequence of the rbcMT cDNA as shown in SEQ. ID. NO: 41. All of the peptic polypeptide sequences obtained from affinity-purified Rubisco LSMT were identified in the translated open-reading frame of the rbcMT cDNA.

The rbcMT cDNA of 1802 bp in length contained a 5' leader of 58-nucleotides which contained several short repeat elements and a 3'-untranslated region of 276-nucleotides. The rbcMT cDNA encoded for a protein of 489-amino acid residues with a predicted molecular mass of 55 kDa. Examination of the amino terminus of Rubisco LSMT revealed several motifs that commonly appear in chloroplast transit-peptide sequences, such as an abundance of hydroxylated amino acids Ser and Thr, presence of small hydrophobic amino acids, and general lack of acidic amino acids (Keegstra et al, "Chloroplastic precursors and their transport across the envelope membranes," *Annu. Rev. Plant. Physiol. Plant. Mol. Biol.* 40: 471–501 (1989); and Theg et al, "Protein import into chloroplasts," *Trends in Cell Biology* 3:186–190 (1993)). Given that N-terminal sequence information could not be obtained for Rubisco LSMT, and that there is as yet no amino acid consensus sequence or secondary structural motif which unambiguously identifies the processing site for removal of chloroplast transit sequences (von Heijne et al, "Chloroplast transit peptides: The perfect random coil?" *FEBS Lett.* 278(1):1–3 (1991)), the cleavage site between the precursor and mature forms of Rubisco LSMT could not be determined.

Comparison of the deduced amino acid sequence of rbcMT cDNA with protein carboxyl methyltransferases from wheat (D-aspartyl/L-isoaspartyl protein methlytransferase, Mudgett et al, "Characterization of plant L-isoaspartyl methyltransferases that may be involved in seed survival: Purification, cloning, and sequence analysis of the wheat germ enzyme," *Biochemistry* 32:11100–11111 (1993)) and *E. coli* (gamma-glutamyl carboxyl methyltransferase, Mutoh et al, "Nucleotide sequence corresponding to five chemotaxis genes in *Escherichia coli,*" *J. Bacteriol.* 165:161–166 (1986)) showed a low alignment score with sequence identity on the order of 10% (gaps in the sequence were introduced to maximize alignment). Three short amino acid regions (8 to 10 residues) of sequence similarity have been reported for several protein and small-molecule AdoMet-dependent methyltransferases (Kagan et al, "Widespread occurrence of three sequence motifs in diverse S-adenosylmethionine-dependent methyltransferases suggests a common structure for these enzymes," *Arch. Biochem. Biophy.* 310(2):417427 (1994)). Using manual alignment, none of the three proposed sequence motifs of AdoMet-dependent methyltransferases were detected in Rubisco rbcMT. In a search of the Swissprot and NBRF-PIR data banks, the best match for Rubisco rbcMT was AfsR protein of *Streptomyces coelicolor which reflected a* 23% sequence identity over the entire protein, again with considerable gaps introduced.

Example 10

DNA analysis

Figure 3:
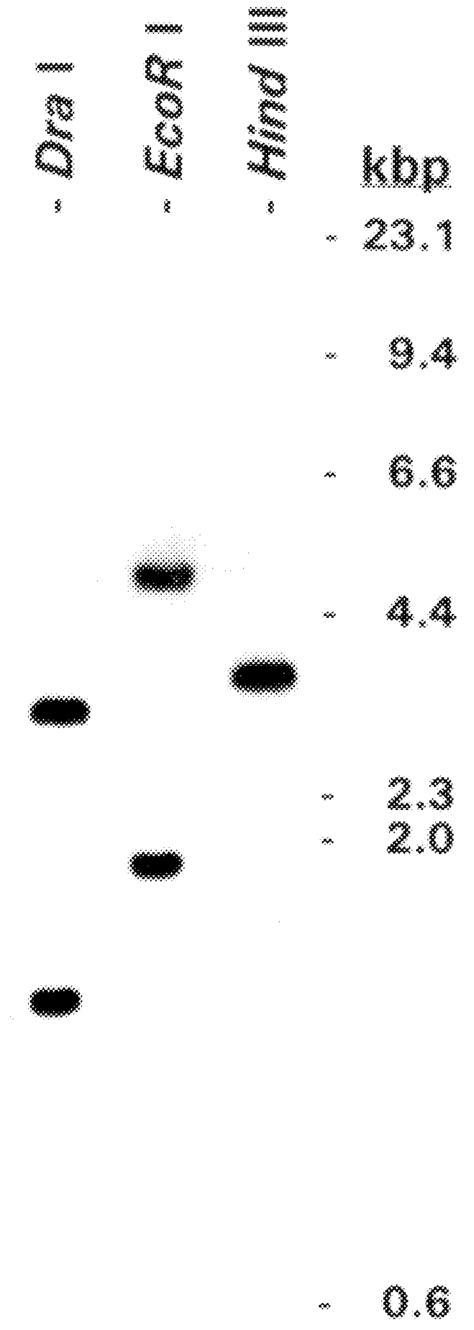
FIG. 3 shows a Southern blot analysis of the rbcMT gene in pea. Ten μg of genomic DNA from pea was digested with EcoR I, Hind III, or Dra I, and electrophoresed on an 0.8% agarose gel. The blot was probed with a 1775 bp rbcMT cDNA of pea. Approximate sizes in kbp are indicated to the left. Blots were exposed to x-ray film for 48 hours.

To obtain information on gene copy number, total pea leaf DNA was isolated and digested with several different restriction endonucleases (FIG. 3). A 1775 bp rbcMT cDNA probe hybridized to two EcoR I DNA fragments, approximately 5.3 kbp and 2.0 kbp (one EcoR I restriction endonuclease site is located within the sequenced cDNA). Two bands, approximately 3.5 kbp and 1.3 kbp, were observed after cleavage with Dra I, while a single band of 3.7 kbp was observed after DNA-digestion with Hind III. The simplicity of the DNA restriction digest pattern suggests that the gene copy number per haploid genome is low for rbcMT.

Example 11

RNA analyses

Figure 4:
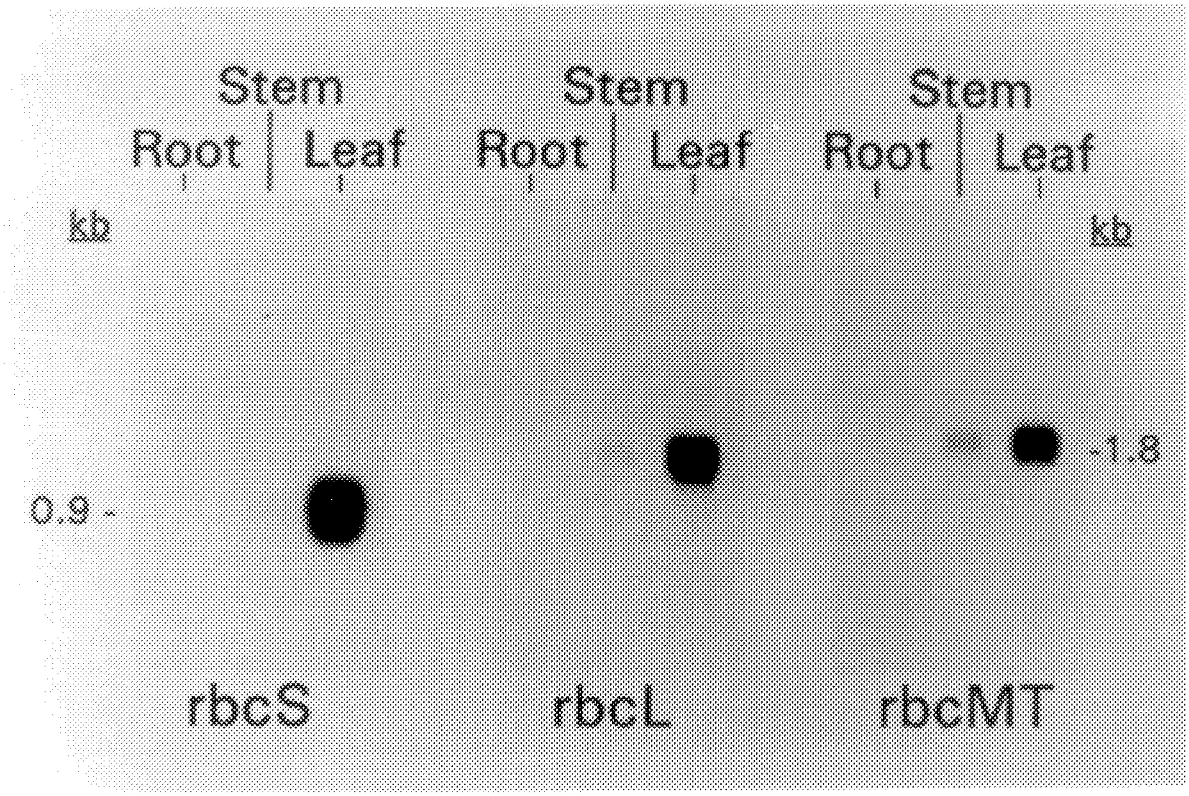
FIG. 4 illustrates organ-specific accumulation of rbcMT mRNA. Messenger-RNA was isolated from roots, stems, and leaves of 10 day old chamber-grown pea. Northern blots were loaded on an equal RNA basis and were probed with radiolabeled antisense RNA to rbcS, rbcL or rbcMT. Northern blots of rbcS, rbcL and rbcMT mRNA were exposed to x-ray film for 2 hours, 1 hour, and 36 hours, respectively.

Northern blot analyses were conducted on pea tissues to examine several developmental and organ-specific parameters governing rbcMT gene expression. As a basis for comparison, the expression of genes encoding Rubisco small (rbcS) and large (rbcL) subunit were concomitantly examined. The rbcS gene family and rbcL gene were examined in an attempt to determine whether the expression of the Rubisco subunits and Rubisco LSMT was coordinated. Northern blot analysis indicated that the rbcMT gene encoded for a single species of mRNA of approximately 1.8 kb in length (see FIG. 4). Examination of organ-specific expression showed that accumulation of the rbcMT transcript paralleled the accumulation of rbcL and rbcS mRNA with the greatest proportion of mRNA being localized in green leaf tissue. Transcripts encoding rbcS, rbcL and rbcMT were detected in pea stems, though the level of expression was 7, 10, and 28-fold lower, respectively, than in green leaves. The quantity of rbcMT, rbcS, and rbcL mRNA in root tissue was below the level of Northern blot sensitivity. Maximum extractable Rubisco LSMT activity generally paralleled the accumulation of rbcMT mRNA, though the enzyme activity detected in stems was greater than would be predicted based on mRNA levels. Maximum extractable Rubisco LSMT activity of roots, stems, and green leaves was 2, 15, and 36 pmoles $CH_3 \cdot min^{-1} \cdot mg$ $proteins^{-1}$, respectively. Finally, it should be noted that the exposure times of the rbcMT, rbcS, and rbcL Northern analyses differ considerably and hence should be considered when comparing the absolute amounts of each transcript. The exposure time of rbcMT Northern analyses were consistently 25- to 50-times longer than that of rbcL or rbcS, suggesting that rbcMT transcripts do not accumulate to the level of the Rubisco subunits.

Figure 5:
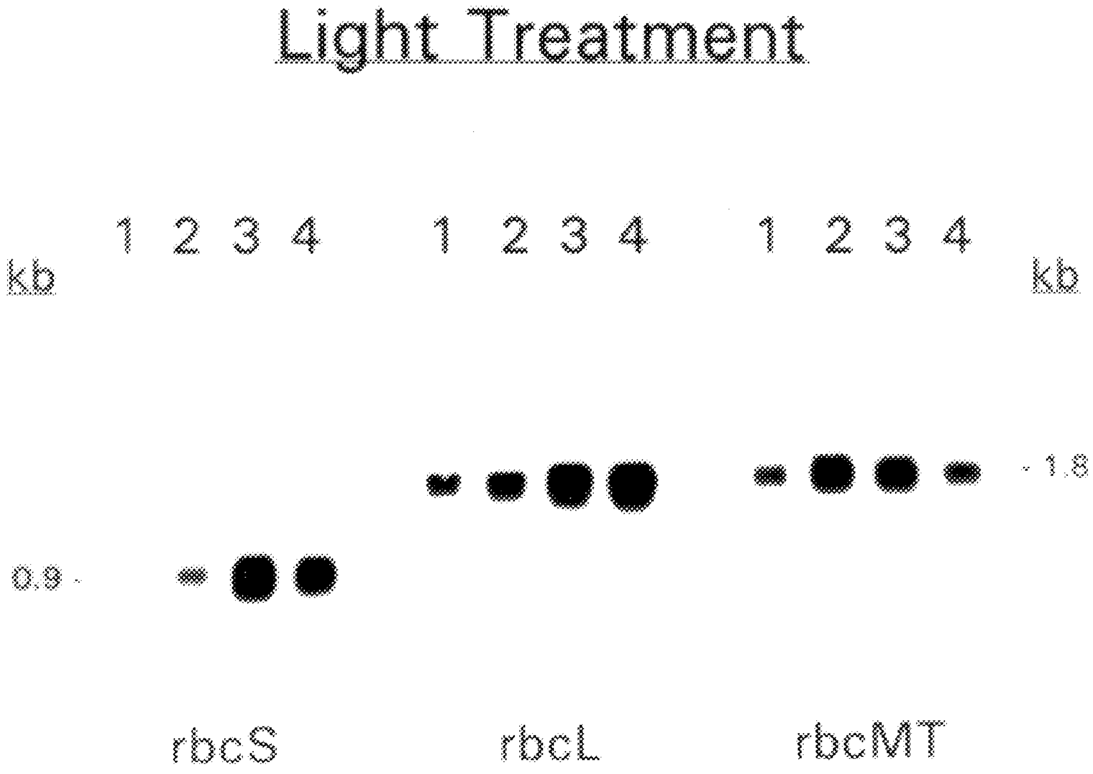
In FIG. 5, light-dependent accumulation of rbcMT mRNA in etiolated pea is shown. Peas were germinated in a dark chamber in a light-tight room. After 8 days, etiolated seedlings were either harvested (treatment 1) or transferred to the light for 24 hours (treatment 2) or 72 hours (treatment 3). Control seedlings were germinated in the light and harvested after 8 days (treatment 4). RNA was isolated from leaf tissue from each treatment and Northern analyses were conducted.

Examination of the accumulation of rbcMT mRNA during the greening of pea leaves is shown in FIG. 5. A low level of rbcMT mRNA was detected in 8-day-old dark-grown pea leaves (lane 1). Upon illumination of etiolated peas, rbcMT transcript levels increased ~3-fold after 24 hours of illumination and then declined slightly after an additional 48 hours of development in the light (lanes 2–3). The maximum extractable activity of Rubisco LSMT enzyme increased during the greening of dark-grown peas from 11 pmoles $CH_3 \cdot min^{-1} \cdot mg\ protein^{-1}$ in dark-grown leaves to an apparent maximum of 32.5 pmoles $CH_3 \cdot min^{-1} \cdot mg\ proteins^{-1}$ after 72 hours illumination. This level of extractable Rubisco LSMT enzyme activity was similar to that observed (32.4 pmoles $CH_3 \cdot min^{-1} \cdot mg\ protein^{-1}$) for peas grown eight days under continuous illumination. Interestingly, the level of rbcMT mRNA in continuous illuminated leaves was significantly lower than the levels observed during the early stages of greening of pea (lanes 2–3 vs. 4). In fact, levels of rbcMT mRNA from continuous illuminated plants was not visibly different from dark-grown leaves. As expected, rbcS and rbcL transcript levels also increased upon illumination of dark-grown seedlings. In contrast to rbcMT, transcripts of rbcS and rbcL reached an apparent maximum during the latter stages of greening (lane 3). In addition, rbcS and rbcL transcript levels remained elevated in leaves grown under continuous illumination (lane 4). These results indicate that, unlike rbcS and rbcL, transcript levels for rbcMT reach an apparent maximum during the early stages of light-induced leaf development and decline in mature light-grown leaf tissue. These changes in transcript levels would be expected for an enzyme whose function involves post-translational protein processing.

All of the references cited herein are effectively incorporated by reference to the same extent as if each individually had been incorporated by reference.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A composition comprising a recombinant Rubisco LSMT enzyme encoded by a Rubisco LSMT gene endogenous to a photosynthesizing plant having a large subunit of Rubisco and which recombinant Rubisco LSMT enzyme composition is devoid of other plant proteins which are expressed by the plant that endogenously expresses said Rubisco LSMT enzyme.

2. A composition comprising a recombinant Rubisco LSMT enzyme which is encoded by a Rubisco LSMT cDNA having the sequence of SEQ ID NO: 41 and which recombinant Rubisco LSMT enzyme composition is devoid of other plant proteins which are expressed by the plant that endogenously expresses said Rubisco LSMT enzyme.

3. A recombinant Rubisco LSMT enzyme produced by the process of transforming a plant which does not endogenously express said Rubisco LSMT enzyme with a vector comprising a Rubisco LSMT gene from a photosynthesizing plant that endogenously expresses said Rubisco LSMT enzyme and expressing said enzyme.

4. A recombinant Rubisco LSMT enzyme produced by the process of transforming a plant which does not endogenously express said Rubisco LSMT enzyme with a vector comprising a Rubisco LSMT cDNA having SEQ ID NO: 41 and expressing said enzyme.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 1
( D ) OTHER INFORMATION: /note= "Amino acid 1 wherein Xaa = NH2."

( i x ) FEATURE:
( A ) NAME/KEY: Modified-site
( B ) LOCATION: 18
( D ) OTHER INFORMATION: /note= "Amino acid 18 wherein Xaa =

COOH.”

( x i ) SEQUENCE DESCRIPTION: SEQ ID NO:1:

Xaa Pro Met Ala Asp Leu Ile Asn His Ser Ala Gly Val Thr Asn Glu
1 5 10 15

Asp Xaa ( 2 ) INFORMATION FOR SEQ ID NO:2:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CCAATGGCAG ATTTAATTAA TCATTCAGCA GGAGTAACAA ATGAAGAT 48

( 2 ) INFORMATION FOR SEQ ID NO:3:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CCCATGGCCG ACTTGATAAA CCACTCCGCC GGCGTCACCA ACGAGGAC 48

( 2 ) INFORMATION FOR SEQ ID NO:4:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

CCGATGGCGG ACCTAATCAA CCACTCGGCG GGGGTGACGA ACGAGGAC 48

( 2 ) INFORMATION FOR SEQ ID NO:5:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

CCTATGGCTG ACCTCATCAA CCACTCTGCT GGTGTTACTA ACGAGGAC 48

( 2 ) INFORMATION FOR SEQ ID NO:6:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

CCTATGGCTG ACCTGATCAA CCACAGTGCT GGTGTTACTA ACGAGGAC 48

( 2 ) INFORMATION FOR SEQ ID NO:7:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

CCTATGGCTG ACCTTATCAA CCACAGCGCT GGTGTTACTA ACGAGGAC 48

( 2 ) INFORMATION FOR SEQ ID NO:8:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..30
( D ) OTHER INFORMATION: /note= "Nucleotides 6, 9, 16, 18, 21, 24, 27 and 30 wherein N = I."

( x i ) SEQUENCE DESCRIPTION: SEQ ID NO:8:

GATTTNATNA ATCATNCNGC NGGNGTNACN AATGAAGAT 39

( 2 ) INFORMATION FOR SEQ ID NO:9:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..30
( D ) OTHER INFORMATION: /note= "Nucleotides 6, 9, 16, 18, 21, 24, 27 and 30 wherein N = I."

( x i ) SEQUENCE DESCRIPTION: SEQ ID NO:9:

GATTTNATNA ATCATNGNGC NGGNGTNACN AACGAGGAC 39

( 2 ) INFORMATION FOR SEQ ID NO:10:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

GGGTACCGTC TAAATTAATT AGTAAGTCGT CCTCATTGTT TACTTCTA 48

( 2 ) INFORMATION FOR SEQ ID NO:11:

( i ) SEQUENCE CHARACTERISTICS:

( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GGCTACCGGC TGAACTATTT GGTGAGGCGG CCGCAGTGGT TGCTCCTG 48

( 2 ) INFORMATION FOR SEQ ID NO:12:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

GGATACCGCC TGGATTAGTT GGTGAGCCGC CCCCACTGCT TGCTCCTG 48

( 2 ) INFORMATION FOR SEQ ID NO:13:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

GGTTACCGAC TGGAGTAGTT GGTGAGACGA CCACAATGAT TGCTCCTG 48

( 2 ) INFORMATION FOR SEQ ID NO:14:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

GGTTACCGAC TGGACTAGTT GGTGTCACGA CCACAATGAT TGCTCCTG 48

( 2 ) INFORMATION FOR SEQ ID NO:15:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

GGTTACCGAC TGGAATAGTT GGTGTCGCGA CCACAATGAT TGCTCCTG 48

( 2 ) INFORMATION FOR SEQ ID NO:16:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 12..36
( D ) OTHER INFORMATION: /note= "Nucleotides 12, 15, 22, 24, 27, 30, 33 and 36 wherein N = I."

( x i ) SEQUENCE DESCRIPTION: SEQ ID NO:16:

T A C C G G C T A G A N T A N T T G G T G N G N C G N C C N C A N T G N T T G 3 9

( 2 ) INFORMATION FOR SEQ ID NO:17:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 12..36
( D ) OTHER INFORMATION: /note= "Nucleotides 12, 15, 22, 24, 27, 30, 33 and 36 wherein N = I."

( x i ) SEQUENCE DESCRIPTION: SEQ ID NO:17:

T A C C G C C T C G A N T A N T T G G T G N C N C G N C C N C A N T G N T T G 3 9

( 2 ) INFORMATION FOR SEQ ID NO:18:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 12..36
( D ) OTHER INFORMATION: /note= "Nucleotides 12, 15, 22, 24, 27, 30, 33 and 36 wherein N = I."

( x i ) SEQUENCE DESCRIPTION: SEQ ID NO:18:

T A C C G A C T C G A N T A N T T G G T G N C N C G N C C N C A N T G N T T G 3 9

( 2 ) INFORMATION FOR SEQ ID NO:19:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 12..36
( D ) OTHER INFORMATION: /note= "Nucleotides 12, 15, 22, 24, 27, 30, 33 and 36 wherein N = I."

( x i ) SEQUENCE DESCRIPTION: SEQ ID NO:19:

T A C C G T C T C G A N T A N T T G G T G N C N C G N C C N C A N T G N T T G 3 9

( 2 ) INFORMATION FOR SEQ ID NO:20:

( i ) SEQUENCE CHARACTERISTICS:
( A ) LENGTH: 16 amino acids

-continued ( B ) TYPE: amino acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 1
( D ) OTHER INFORMATION: /note= "Amino acid 1 wherein Xaa = NH2."

( i x ) FEATURE:
( A ) NAME/KEY: Modified-site
( B ) LOCATION: 16
( D ) OTHER INFORMATION: /note= "Amino acid 16 wherein Xaa = COOH."

( x i ) SEQUENCE DESCRIPTION: SEQ ID NO:20:

```
Xaa Tyr Asn Arg Thr Leu Pro Pro Gly Leu Leu Pro Tyr Leu Arg Xaa
1               5                   10                  15
```

( 2 ) INFORMATION FOR SEQ ID NO:21:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

TATAATCGAA CATTACCACC AGGATTATTA CCATATTTAC GA 42

( 2 ) INFORMATION FOR SEQ ID NO:22:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

TACAACCGCA CCTTGCCCCC CGGCTTGTTG CCCTACTTGC GC 42

( 2 ) INFORMATION FOR SEQ ID NO:23:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

TACAACCGGA CGCTACCGCC GGGGCTACTA CCGTACCTAC GG 42

( 2 ) INFORMATION FOR SEQ ID NO:24:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

-continued

TACAACCGTA CTCTCCCTCC TGGTCTCCTC CCTTACCTCC GT 42

( 2 ) INFORMATION FOR SEQ ID NO:25:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

TACAACAGAA CTCTGCCTCC TGGTCTGCTG CCTTACCTGA GA 42

( 2 ) INFORMATION FOR SEQ ID NO:26:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

TACAACAGGA CTCTTCCTCC TGGTCTTCTT CCTTACCTTA GG 42

( 2 ) INFORMATION FOR SEQ ID NO:27:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..27
( D ) OTHER INFORMATION: /note= "Nucleotides 6, 9, 12, 15, 18, 21, 24 and 27 wherein N = I."

( x i ) SEQUENCE DESCRIPTION: SEQ ID NO:27:

AATCGNACNT TNCCNCCNGG NTTNTTNCCA TATTT 35

( 2 ) INFORMATION FOR SEQ ID NO:28:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..27
( D ) OTHER INFORMATION: /note= "Nucleotides 6, 9, 12, 15, 18, 21, 24 and 27 wherein N = I."

( x i ) SEQUENCE DESCRIPTION: SEQ ID NO:28:

AATAGNACNT TNCCNCCNGG NTTNTTNCCC TACCT 35

( 2 ) INFORMATION FOR SEQ ID NO:29:

( i ) SEQUENCE CHARACTERISTICS:
( A ) LENGTH: 35 base pairs

-continued ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..27
( D ) OTHER INFORMATION: /note= "Nucleotides 6, 9,. 12, 15, 18, 21, 24 and 27 wherein N = I."

( x i ) SEQUENCE DESCRIPTION: SEQ ID NO:29:

AATAGNACNT TNCCNCCNGG NTTNTTNCCG TACCT 35

( 2 ) INFORMATION FOR SEQ ID NO:30:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..27
( D ) OTHER INFORMATION: /note= "Nucleotides 6, 9, 12, 15, 18, 21, 24 and 27 wherein N = I."

( x i ) SEQUENCE DESCRIPTION: SEQ ID NO:30:

AATAGNACNT TNCCNCCNGG NTTNTTNCCT TACCT 35

( 2 ) INFORMATION FOR SEQ ID NO:31:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:31:

ATATTAGCTT GTAATGGTGG TCCTAATAAT GGTATAAATG CT 42

( 2 ) INFORMATION FOR SEQ ID NO:32:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:32:

ATGTTGGCGT GGAACGGGGG GCCGAACAAC GGGATGAACG CG 42

( 2 ) INFORMATION FOR SEQ ID NO:33:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:33:

-continued

ATGTTGGCCT GCGATGGCGG CCCCGATGAT GGCATGGATG CC 42

( 2 ) INFORMATION FOR SEQ ID NO:34:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:34:

ATGTTGGCAT GAGAGGGAGG ACCAGAGGAG GGAATGGAGG CA 42

( 2 ) INFORMATION FOR SEQ ID NO:35:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:35:

ATGTTGTCTT GAGACGGAGG ACCAGACGAC GGAATGGACT CT 42

( 2 ) INFORMATION FOR SEQ ID NO:36:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:36:

ATGTTGTCCT GAGAAGGAGG ACCAGAAGAA GGAATGGAAT CC 42

( 2 ) INFORMATION FOR SEQ ID NO:37:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 9..33
( D ) OTHER INFORMATION: /note= "Nucleotides 9, 12, 15, 18, 21, 24, 27, 30 and 33 wherein N = I."

( x i ) SEQUENCE DESCRIPTION: SEQ ID NO:37:

ATATTAGCNT GNGANGGNGG NCCNGANGAN GGNATG 36

( 2 ) INFORMATION FOR SEQ ID NO:38:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:

-continued ( A ) NAME/KEY: misc_feature
( B ) LOCATION: 9..33
( D ) OTHER INFORMATION: /note= "Nucleotides 9, 12, 15, 18, 21, 24, 27, 30 and 33 wherein N = I."

( x i ) SEQUENCE DESCRIPTION: SEQ ID NO:38:

ATGTTGTCNT GNGANGGNGG NCCNGANGAN GGNATG 36

( 2 ) INFORMATION FOR SEQ ID NO:39:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:39:

CCAAAAGAAG TCATCCAGCG TCAC 24

( 2 ) INFORMATION FOR SEQ ID NO:40:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:40:

CAUCAUCAUC AUCCTGTGGC AGAATACCAA AATAGT 36

( 2 ) INFORMATION FOR SEQ ID NO:41:

( i ) SEQUENCE CHARACTERISTICS:
( A ) LENGTH: 1801 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 59..1528

( x i ) SEQUENCE DESCRIPTION: SEQ ID NO:41:

```
ACAACACAAA AGAAAAGCGT ATTATCACAA AACAAAACCA AGAACTAGAA ACCAGAAA       58

ATG GCT ACT ATC TTT TCC GGA GGT TCA GTT TCT CCC TTT CTT TTT CAC      106
Met Ala Thr Ile Phe Ser Gly Gly Ser Val Ser Pro Phe Leu Phe His
  1               5                  10                  15

ACC AAC AAG GGT ACA TCT TTT ACA CCC AAA GCT CCA ATT CTT CAT CTC      154
Thr Asn Lys Gly Thr Ser Phe Thr Pro Lys Ala Pro Ile Leu His Leu
             20                  25                  30

AAG AGA TCT TTC TCT GCA AAA TCA GTA GCC TCT GTA GGA ACC GAA CCA      202
Lys Arg Ser Phe Ser Ala Lys Ser Val Ala Ser Val Gly Thr Glu Pro
         35                  40                  45

TCA CTG TCT CCA GCA GTT CAA ACC TTC TGG AAG TGG CTA CAG GAA GAA      250
Ser Leu Ser Pro Ala Val Gln Thr Phe Trp Lys Trp Leu Gln Glu Glu
     50                  55                  60

GGT GTC ATC ACT GCA AAG ACC CCA GTG AAA GCT AGT GTG GTC ACA GAA      298
Gly Val Ile Thr Ala Lys Thr Pro Val Lys Ala Ser Val Val Thr Glu
 65                  70                  75                  80

GGT TTA GGA TTG GTT GCA CTT AAG GAC ATT TCT AGG AAT GAT GTT ATT      346
Gly Leu Gly Leu Val Ala Leu Lys Asp Ile Ser Arg Asn Asp Val Ile
```

-continued

```
                            85                       90                       95

TTG CAG GTA CCA AAA AGG CTG TGG ATA AAT CCA GAT GCA GTT GCA GCT     394
Leu Gln Val Pro Lys Arg Leu Trp Ile Asn Pro Asp Ala Val Ala Ala
            100                     105                     110

TCA GAG ATT GGG AGA GTG TGC AGT GAG TTG AAG CCA TGG TTG TCT GTT     442
Ser Glu Ile Gly Arg Val Cys Ser Glu Leu Lys Pro Trp Leu Ser Val
        115                     120                     125

ATA CTC TTT CTT ATA AGA GAG AGG TCA AGG GAA GAT TCT GTT TGG AAG     490
Ile Leu Phe Leu Ile Arg Glu Arg Ser Arg Glu Asp Ser Val Trp Lys
    130                     135                     140

CAC TAT TTT GGT ATT CTG CCA CAG GAA ACT GAT TCT ACT ATA TAT TGG     538
His Tyr Phe Gly Ile Leu Pro Gln Glu Thr Asp Ser Thr Ile Tyr Trp
145                     150                     155                     160

TCA GAG GAA GAG CTT CAA GAG CTT CAA GGT TCT CAA CTT TTG AAA ACA     586
Ser Glu Glu Glu Leu Gln Glu Leu Gln Gly Ser Gln Leu Leu Lys Thr
                165                     170                     175

ACA GTG TCT GTG AAA GAA TAT GTG AAG AAT GAA TGT TTG AAA CTA GAA     634
Thr Val Ser Val Lys Glu Tyr Val Lys Asn Glu Cys Leu Lys Leu Glu
            180                     185                     190

CAA GAA ATC ATT CTC CCT AAT AAG CGG CTT TTT CCG GAT CCT GTG ACG     682
Gln Glu Ile Ile Leu Pro Asn Lys Arg Leu Phe Pro Asp Pro Val Thr
        195                     200                     205

CTG GAT GAC TTC TTT TGG GCA TTT GGA ATT CTC AGA TCA AGG GCG TTT     730
Leu Asp Asp Phe Phe Trp Ala Phe Gly Ile Leu Arg Ser Arg Ala Phe
    210                     215                     220

TCT CGC CTT CGC AAT GAA AAT CTG GTT GTG GTT CCA ATG GCA GAC TTG     778
Ser Arg Leu Arg Asn Glu Asn Leu Val Val Val Pro Met Ala Asp Leu
225                     230                     235                     240

ATT AAC CAC AGT GCA GGA GTT ACT ACA GAG GAT CAT GCT TAT GAA GTT     826
Ile Asn His Ser Ala Gly Val Thr Thr Glu Asp His Ala Tyr Glu Val
                245                     250                     255

AAA GGA GCA GCT GGC CTT TTC TCT TGG GAT TAC CTA TTT TCC TTA AAG     874
Lys Gly Ala Ala Gly Leu Phe Ser Trp Asp Tyr Leu Phe Ser Leu Lys
            260                     265                     270

AGC CCC CTT TCC GTC AAG GCC GGA GAA CAG CTA TAT ATA CAA TAT GAT     922
Ser Pro Leu Ser Val Lys Ala Gly Glu Gln Leu Tyr Ile Gln Tyr Asp
        275                     280                     285

TTG AAC AAA AGC AAT GCA GAG TTG GCT CTA GAC TAC GGT TTC ATT GAA     970
Leu Asn Lys Ser Asn Ala Glu Leu Ala Leu Asp Tyr Gly Phe Ile Glu
    290                     295                     300

CCA AAT GAA AAT CGA CAT GCA TAC ACT CTG ACG CTG GAG ATA TCT GAG    1018
Pro Asn Glu Asn Arg His Ala Tyr Thr Leu Thr Leu Glu Ile Ser Glu
305                     310                     315                     320

TCG GAC CCT TTT TTT GAT GAC AAA CTA GAC GTT GCT GAG TCC AAT GGT    1066
Ser Asp Pro Phe Phe Asp Asp Lys Leu Asp Val Ala Glu Ser Asn Gly
                325                     330                     335

TTT GCT CAG ACA GCG TAC TTT GAC ATC TTC TAT AAT CGC ACT CTT CCA    1114
Phe Ala Gln Thr Ala Tyr Phe Asp Ile Phe Tyr Asn Arg Thr Leu Pro
            340                     345                     350

CCT GGA TTG CTT CCA TAT CTG AGA CTT GTA GCG CTA GGG GGT ACC GAC    1162
Pro Gly Leu Leu Pro Tyr Leu Arg Leu Val Ala Leu Gly Gly Thr Asp
        355                     360                     365

GCT TTC TTA TTG GAA TCA CTG TTC AGA GAC ACC ATA TGG GGT CAT CTT    1210
Ala Phe Leu Leu Glu Ser Leu Phe Arg Asp Thr Ile Trp Gly His Leu
    370                     375                     380

GAG TTG TCT GTC AGC CGT GAC AAT GAG GAG CTA CTA TGC AAA GCC GTT    1258
Glu Leu Ser Val Ser Arg Asp Asn Glu Glu Leu Leu Cys Lys Ala Val
385                     390                     395                     400

CGA GAA GCC TGC AAA TCT GCC CTT GCT GGT TAT CAT ACA ACC ATT GAA    1306
Arg Glu Ala Cys Lys Ser Ala Leu Ala Gly Tyr His Thr Thr Ile Glu
```

-continued

```
                        405                           410                           415

CAG GAT CGC GAG TTG AAA GAA GGA AAT CTA GAT TCA AGG CTT GCA ATA      1354
Gln Asp Arg Glu Leu Lys Glu Gly Asn Leu Asp Ser Arg Leu Ala Ile
            420                 425                 430

GCA GTT GGA ATA AGA GAA GGG GAA AAG ATG GTC CTG CAG CAA ATT GAC      1402
Ala Val Gly Ile Arg Glu Gly Glu Lys Met Val Leu Gln Gln Ile Asp
        435                 440                 445

GGG ATC TTC GAG CAG AAA GAA TTG GAG TTG GAC CAG TTA GAG TAT TAT      1450
Gly Ile Phe Glu Gln Lys Glu Leu Glu Leu Asp Gln Leu Glu Tyr Tyr
    450                 455                 460

CAA GAA AGG AGG CTC AAG GAT CTT GGA CTT TGC GGA GAA AAT GGC GAT      1498
Gln Glu Arg Arg Leu Lys Asp Leu Gly Leu Cys Gly Glu Asn Gly Asp
465                 470                 475                 480

ATC CTT GGA GAC CTA GGA AAA TTC TTC TAA TCTTGCAGGA AAATTCTTCT        1548
Ile Leu Gly Asp Leu Gly Lys Phe Phe  *
                485                 490

AATCTTGCAG GAAGCATTTC AACCTGTTAA AGATACACTG TTGTTTACAA ATGGAGTCTT    1608

CTGAGACGTA CGATGCCATG ATTTTGCAAT CAATCTTAAG AGGATCGTGA TCAATTTTGA    1668

CTCTGGAGTC TGGACCAATC CATTACATGC TTGAAGTTTG TAAAGAGGAA AATGTAATGT    1728

GTGAAATATA AATTACACTT CTGTACTGGT GATTATTTAT AAAGCAGTTG ACCATTATTA    1788

TTACAAAAAA AAA                                                       1801
```